US010072242B2

(12) United States Patent
Kanemura et al.

(10) Patent No.: US 10,072,242 B2
(45) Date of Patent: Sep. 11, 2018

(54) CELL SORTING METHOD

(71) Applicant: FOUNDATION FOR BIOMEDICAL RESEARCH AND INNOVATION AT KOBE, Kobe (JP)

(72) Inventors: Hoshimi Kanemura, Kobe (JP); Masahiro Go, Kobe (JP); Shin Kawamata, Kobe (JP); Naoki Nishishita, Kobe (JP)

(73) Assignee: Foundation for Biomedical Research and Innovation at Kobe, Kobe (JP)

( * ) Notice: Subject to any disclaimer, the term of this patent is extended or adjusted under 35 U.S.C. 154(b) by 3 days.

(21) Appl. No.: 14/780,324

(22) PCT Filed: Mar. 25, 2014

(86) PCT No.: PCT/JP2014/058373
§ 371 (c)(1),
(2) Date: Sep. 25, 2015

(87) PCT Pub. No.: WO2014/157257
PCT Pub. Date: Oct. 2, 2014

(65) Prior Publication Data
US 2016/0040123 A1 Feb. 11, 2016

(30) Foreign Application Priority Data
Mar. 25, 2013 (JP) .................... 2013-062765

(51) Int. Cl.
*C12N 5/00* (2006.01)
*C12N 5/074* (2010.01)
*A61K 35/545* (2015.01)

(52) U.S. Cl.
CPC .......... *C12N 5/0081* (2013.01); *A61K 35/545* (2013.01); *C12N 5/0696* (2013.01)

(58) Field of Classification Search
None
See application file for complete search history.

(56) References Cited

U.S. PATENT DOCUMENTS

2006/0018886 A1* 1/2006 Klimanskaya ......... A61K 35/44
424/93.7

FOREIGN PATENT DOCUMENTS

| WO | WO 2011/063005 A2 | 5/2011 |
| WO | WO 2011/158960 A1 | 12/2011 |
| WO | WO 2012/078153 A1 | 6/2012 |
| WO | WO 2012/133674 A1 | 10/2012 |

OTHER PUBLICATIONS

Bharti et al., The new paradigm: retinal pigment epithelium cells generated from embryonic or induced pluripotent stem cells, Pigment Cell Melanoma Res. Feb. 2011; 24(1): 21-34.*

Qiu et al., Lin28-mediated post-transcriptional regulation of Oct4 expression in human embryonic stem cells, Nucleic Acids Research, 2010, vol. 38, No. 4, Published online Dec. 4, 2009, pp. 1240-1248.*
Stellmach et al., Prevention of ischemia-induced retinopathy by the natural ocular antiangiogenic agent pigment epithelium-derived factor, PNAS, Feb. 27, 2001, vol. 98, No. 5, pp. 2593-2597.*
Zhu et al, Polarized Secretion of PEDF from Human Embryonic Stem Cell—Derived RPE Promotes Retinal Progenitor Cell Survival, Investigative Ophthalmology & Visual Science, Mar. 2011, vol. 52, No. 3.*
Elahy et al., The Emerging Role of PEDF in StemCell Biology, Journal of Biomedicine and Biotechnology vol. 2012, Article ID 239091, 6 pages.*
Sagheer et al., Pigment Epithelium-Derived Factor (PEDF) is a Determinant of Stem Cell Fate: Lessons from an Ultra-Rare Disease, J. Dev. Biol. 2015, 3, 112-128; doi:10.3390/jdb3040112.*
Klimanskaya et al., Derivation and Comparative Assessment of Retinal Pigment Epithelium from Human Embryonic Stem Cells Using Transcriptomics, Cloning and Stem Cells vol. 6, No. 3, 2004.*
Broadhead et al., Cancer cell apoptotic pathways mediated by PEDF: prospects for therapy, Trends in Molecular Medicine vol. 15 No. 10, 2009.*
Klimanskaya et al., Derivation and Comparative Assessment of Retinal Pigment Epithelium from Human Embryonic Stem Cells Using Transcriptomics, Cloning and Stem Cells, vol. 6, No. 3, 2004.*
Cai et al., *The Journal of Biological Chemistry*, 281(6): 3604-3613 (2006).
Chandolu et al., *Journal of Biomedicine and Biotechnology*, Article ID 740295 (2012).
Chen et al., *Biochemical and Biophysical Research Communications*, 348(4): 1288-1295 (2006).
Garcia et al., *Cancer Research*, 64(16): 5632-5642 (2004).
Ho et al., *Cardiovascular Research*, 76(2): 213-223 (2007).
Ho et al., *Cardiovascular Research*, 78(1): 199 (2008).

(Continued)

*Primary Examiner* — Taeyoon Kim
*Assistant Examiner* — Srikanth Patury
(74) *Attorney, Agent, or Firm* — Leydig, Voit & Mayer, Ltd.

(57) ABSTRACT

The invention provides a method of removing or reducing undifferentiated cells from a differentiated cell population contaminated or having a risk of contamination with undifferentiated cells by contacting a pigment epithelium-derived factor with the differentiated cell population to induce apoptosis of the undifferentiated cells. The invention also provides an agent for cell transplantation therapy, containing a differentiated cell population substantially free of an undifferentiated cell, which is obtained by the method, as well as an agent for inducing apoptosis of an undifferentiated cell, containing a pigment epithelium-derived factor, and combined use of the aforementioned agent for cell transplantation therapy and the aforementioned agent for inducing apoptosis.

18 Claims, 14 Drawing Sheets

Specification includes a Sequence Listing.

(56) References Cited

OTHER PUBLICATIONS

Huang et al., *Environmental Toxicology*, 28(4): 190-200 (2011).
Kanemura et al., *Scientific Reports*, 3: 2334 (2013).
Kuroda et al., *PLoS One*, 7(5): e37342 (2012).
Lee et al., *Journal of Cellular Physiology*, 216(1): 269-275 (2008).
Lee et al., *Toxicology in Vitro*, 27(1): 492-498 (2012).
Notari et al., *The Journal of Biological Chemistry*, 281(49): 38022-38037 (2006).
Japanese Patent Office, International Search Report in International Application No. PCT/JP2014/058373 (dated Jun. 24, 2014) English translation.
Japanese Patent Office, Written Opinion in International Application No. PCT/JP2014/058373 (dated Jun. 24, 2014) English translation.
Tombran-Tink, *Frontiers in Bioscience*, 10: 2131-2149 (2005).
Zhu et al., *Investigative Ophthalmology & Visual Science*, 52(3): 1573-1585 (2011).
European Patent Office, Extended European Search Report in European Patent Application No. 14773935.3 (dated Aug. 5, 2016).

\* cited by examiner

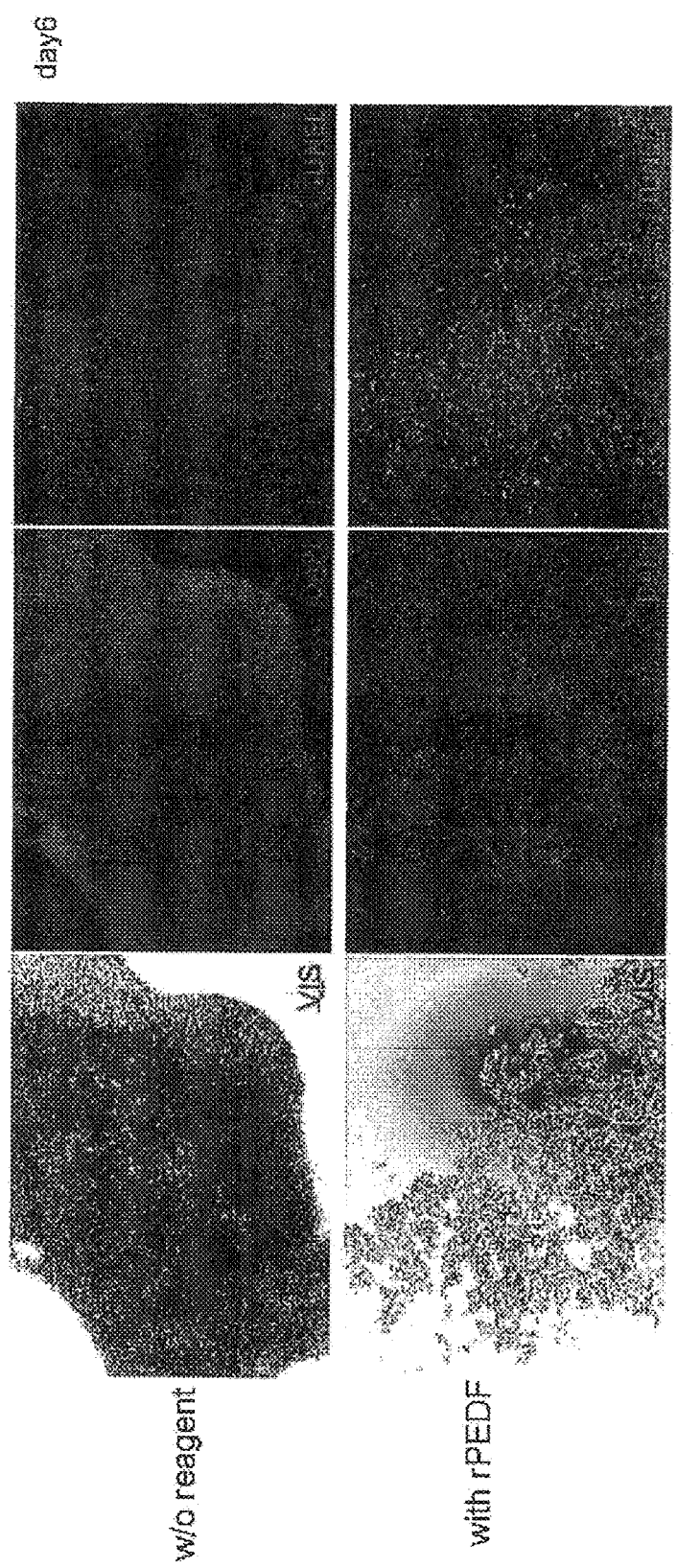

CELL SORTING METHOD

CROSS-REFERENCE TO RELATED APPLICATIONS

This patent application is the U.S. national phase of International Patent Application No. PCT/JP2014/058373, filed Mar. 25, 2014, which claims the benefit of Japanese Patent Application No. 2013-062765, filed on Mar. 25, 2013, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 9,992 bytes ASCII (Text) file named "721924SequenceListing.txt," created Sep. 23, 2015.

TECHNICAL FIELD

The present invention relates to a method of sorting cells, more specifically, a method of sorting/purifying differentiated cells by removing or reducing undifferentiated cells from a differentiated cell population contaminated or having a risk of contamination with undifferentiated cells. The present invention also relates to an undifferentiated cell elimination agent for the aforementioned method, and an agent for a cell transplantation therapy, which is obtained by the aforementioned method, composed of tumorigenicity risk-free, uniform and safe differentiated cells.

BACKGROUND ART

Clinical application of regenerative medicines has been studied recently, and induction of differentiation of pluripotent stem cells such as iPS cell and ES cell into desired cells has been actively pursued. In fact, clinical tests using ES cell-derived RPE (retinal pigment epithelium) cell for Stargardt disease and dry age-related macular degeneration has already been started. In addition, clinical tests using autologous iPS cell (iPSC)-derived RPE cell for wet age-related macular degeneration are designed by some groups.

However, pluripotent stem cells such as iPS cell and ES cell often show canceration during their growth, and differentiated cells derived from pluripotent stem cell need to be carefully evaluated for the presence or absence of tumor formation caused by the remaining undifferentiated iPS cell and ES cell. This poses the largest problem in transplantation of autologous iPSC-derived cells and tissues free of immunological barriers. That is, it is extremely important for practicalization of differentiation-induced cells and tissues to remove remaining undifferentiated cells and purify differentiated cells. The present inventors reported a method of highly sensitively detecting iPS cells remaining in iPSC-derived RPE cells (non-patent document 1). However, a method of more efficiently removing remaining undifferentiated cells in vitro has been desired.

In the meantime, cytokine, extracellular matrix, complement factor and the like secreted by pluripotent stem cells and differentiated cells derived therefrom have also been studied. Of these, PEDF (pigment epithelium-derived factor) is a 50 kDa secreted protein also known as Serpin F1, which was found as a protein secreted by RPE cell, and is a factor having an angiogenesis suppressive action (non-patent document 2) and a neuroprotection action (non-patent document 3). Secretion of PEDF is found not only in RPE cells but also adipocytes, hepatocytes and dendritic cells (BioGPS site). Also, PEDF is known to induce apoptosis in cancer cells (non-patent document 4), vascular endothelial cells (non-patent document 5) and human umbilical vein endothelial cells (HUVEC) (non-patent document 6) and, as induction pathways of these apoptosis, FAS/FASL pathway (non-patent document 4) and p38 MAPK pathway can be mentioned (non-patent document 5). However, a direct influence of PEDF on undifferentiated cells has not been known well.

DOCUMENT LIST

Non-Patent Documents non-patent document 1: Kuroda T. et al., PLoS ONE, 7(5): e37342 (2012)
non-patent document 2: Notari, L. et al., J. Biol. Chem., 281(49): 38022-37 (2006)
non-patent document 3: Cai, J. et al., J. Biol. Chem., 281(6): 3604-13 (2006)
non-patent document 4: Cancer Res., 64(16): 5632-42 (2004)
non-patent document 5: Chen, L. et al., Biochem. Biophys. Res. Commun. 348(4): 1288-95 (2006)
non-patent document 6: Cardiovasc. Res., 78(1): 199 (2008)

SUMMARY OF THE INVENTION

Problems to be Solved by the Invention

While various cell sorting methods such as a method of applying FACS and the like have been proposed, a method for sorting differentiated cells and undifferentiated cells easily at a low cost has been demanded.

Means of Solving the Problems

The present inventors have found that PEDF secreted by RPE cells inhibits growth of iPS cells and induce apoptosis. This phenomenon was observed in co-culture with RPE cell, as well as by administration of recombinant PEDF (rPEDF). Furthermore, the present inventors have found that p38 MAPK is involved in a part of the pathway of the apoptosis and that similar apoptosis is observed in ES cells as well.

Based on these findings, the present inventors further conducted intensive studies and completed the present invention.

Accordingly, the present invention is as described below.

[1] A method of removing or reducing undifferentiated cells from a differentiated cell population contaminated or having a risk of contamination with undifferentiated cells, comprising contacting a pigment epithelium-derived factor with the differentiated cell population.
[2] The method of the above-mentioned [1], wherein the undifferentiated cell is a pluripotent stem cell having differentiation potency into three germ layer lineages.
[3] The method of the above-mentioned [2], wherein the undifferentiated cell further expresses one or more undifferentiated markers selected from the group consisting of Lin28, Oct3/4 and Nanog.
[4] The method of any of the above-mentioned [1]-[3], wherein the undifferentiated cell is an iPS cell or an ES cell.

[5] The method of any of the above-mentioned [1]-[4], which induces apoptosis of undifferentiated cells.
[6] The method of any of the above-mentioned [1]-[4], which does not induce apoptosis of a differentiated cell.
[7] The method of the above-mentioned [6], wherein the differentiated cell is a differentiated cell other than a vascular endothelial cell.
[8] The method of any of the above-mentioned [1]-[7], wherein the differentiated cell population is obtained by differentiation induction of undifferentiated cells.
[9] An agent for cell transplantation therapy, comprising a differentiated cell population substantially free of an undifferentiated cell obtained by the method of any of the above-mentioned [1]-[8].
[10] An agent for inducing apoptosis of an undifferentiated cell, comprising a pigment epithelium-derived factor.
[11] The agent of the above-mentioned [10], wherein the undifferentiated cell is a pluripotent stem cell having differentiation potency into three germ layer lineages.
[12] The agent of the above-mentioned [11], wherein the undifferentiated cell further expresses one or more undifferentiated markers selected from the group consisting of Lin28, Oct3/4 and Nanog.
[13] The agent of any of the above-mentioned [10]-[12], wherein the undifferentiated cell is an iPS cell or an ES cell.
[14] The agent of any of the above-mentioned [10]-[13], which does not induce apoptosis of a differentiated cell.
[15] The agent of the above-mentioned [14], wherein the differentiated cell is a differentiated cell other than a vascular endothelial cell.
[16] The agent of the above-mentioned [9], comprising the agent of any of the above-mentioned [10]-[15] in combination.

Effect of the Invention

According to the present invention, since an undifferentiated cell contaminating a differentiated cell population can be eliminated without sorting from differentiated cells, the differentiated cell can be purified easily at a low cost. Since the thus-obtained differentiated cell population substantially free of an undifferentiated cell can be a safe source of cells for transplantation having a reduced risk of tumorigenicity.

BRIEF DESCRIPTION OF THE DRAWINGS

FIG. 2-1 shows that co-culture with iPS cell-derived RPE cell inhibits growth of iPS cell. (A) is a schematic showing of co-culture of iPS cell and RPE cell. (B) iPS cell was maintained in a matrigel-coated culture insert, and co-cultured in an iPS cell medium with iPSC-derived RPE cell seeded on the bottom of the dish. Phase contrast images of iPS cell 253G1 cultured alone (upper panel) or co-cultured with 253G1-derived RPE cell (lower panel) in 12-transwell on days 2, 4, 6 and 8 of culture are shown. (C) shows growth curves of iPS clone 253G1 co-cultured with 253G1 cell-derived RPE cell, or cultured alone. The cell numbers of iPS clone 253G1 in 12-transwell culture on days 0, 4, 8 and 12 were counted. The mean of 3 independent experiments was plotted, and shown in a line graph with an error bar showing the standard deviation.

FIG. 2-2 shows that co-culture with iPS cell-derived RPE cell induces apoptosis of iPS cell. (D) Apoptotic cell death was examined by TUNEL assay and visualized as a green spot (in circles) (day 6 of culture). (E) shows percentage of TUNEL positive cells to DAPI positive cells of 253G1 cells cultured alone or co-cultured with 253G1-derived RPE cell. The results show mean and standard deviation (error bar) of 4 independent experiments. (F) 253G1 cell co-cultured with 253G1 cell-derived RPE cell markedly impaired the expression of undifferentiated marker Oct3/4 on day 6 of culture. On day 6 of culture, the cells were fixed, stained with an antibody to Oct3/4, and visualized with the secondary antibody Alexa488 (green, right panel). The nucleus was stained with DAPI (blue, left panel). (G) The mRNA levels of Lin28, Oct3/4 and Nanog in 253G1 co-cultured with 253G1-derived RPE cell were measured by quantitative RT-PCR. Using GAPDH as the internal standard, the mRNA levels of the 3 genes were normalized. The results of 3 independent experiments are shown. A decrease rate (mean) from each mRNA level in 253G1 cells cultured alone is shown along with the standard deviation (error bar).

FIG. 4-1 shows that iPS cell death induced by co-culture with RPE cell is blocked by the addition of an anti-PEDF antibody. (A) shows Western blot using anti-PEDF antibody in 253G1 conditioned medium (253G1 sup) and 253G1-derived RPE conditioned medium (253G1 derived-RPE sup). An iPS cell medium alone and recombinant PEDF were used as negative control and positive control, respectively. PEDF detected by anti-PEDF antibody is shown with an arrow. (B) PEDF level in primary RPE cells or conditioned medium of 253G1-derived RPE cells was measured by ELISA. The mean and standard deviation (error bar) of 3 independent experiments are shown. (C) shows phase contrast images of iPS clone 253G1 co-cultured with 253G1-derived RPE cell in the presence of control IgG1 (upper panel) or anti-PEDF antibody (lower panel) on days 2, 4, 6 and 8 of culture.

FIG. 4-2 shows that iPS cell death induced by co-culture with RPE cell is blocked by the addition of an anti-PEDF antibody. (D) The cell number of iPS clone 253G1 co-cultured with 253G1-derived RPE cell in the presence of control IgG1 or anti-PEDF antibody was counted on day 6 of culture, and shown in a proportion to the cell number of 253G1 cultured alone without reagents. The mean and standard deviation (error bar) of 4 independent experiments are shown. (E) apoptotic cell death of iPS clone 253G1 co-cultured with 253G1-derived RPE cell in the presence of control IgG1 (middle panel) or anti-PEDF antibody (lower panel) on day 6 of culture was examined by TUNEL assay and visualized as a green spot (in circles). iPS clone 253G1 (upper panel) cultured alone without reagents was used as control. (F) shows percentage of TUNEL assay positive cells relative to DAPI positive cells on day 6 of culture of 253G1 co-cultured with 253G1-derived RPE cell in the presence of control IgG1 or anti-PEDF antibody. The mean and standard deviation (error bar) of 4 independent experiments are shown.

FIG. 4-3 (G) 253G1 cell co-cultured with 253G1 cell-derived RPE cell markedly impaired the expression of undifferentiated marker Oct3/4 on day 6 of culture. On day 6 of culture, the cells were fixed, stained with an antibody to Oct3/4, and visualized with the secondary antibody Alexa488 (green, right panel). The nucleus was stained with DAPI (blue, left panel). (H) The mRNA levels of Lin28, Oct3/4 and Nanog in 253G1 cells co-cultured with 253G1-derived RPE cell in the presence of control IgG1 or anti-PEDF antibody were measured by quantitative RT-PCR. Using GAPDH as the internal standard, the expression level of mRNA was normalized. The results of 3 independent experiments are shown. A decrease rate (mean) from each mRNA level in 253G1 cells cultured alone without reagent is shown along with the standard deviation (error bar).

FIG. 5-1 shows that recombinant PEDF (rPEDF) induces apoptotic cell death of iPS cell. (A) shows phase contrast images of iPS clone 253G1 cultured in the presence or absence of rPEDF (50 µg/ml) on day 4 of culture. (B) shows changes in the cell number of iPS clone 253G1 cultured in the presence or absence of rPEDF (50 µg/ml) on day 4 of culture as a proportion relative to the cell number at the start of the culture. The results of 3 independent experiments are shown in mean and standard deviation (error bar). (C) Apoptotic cell death of iPS clone 253G1 cultured in the presence or absence of rPEDF (50 µg/ml) was examined on day 4 of culture by TUNEL assay and visualized as a green spot (in circles) (right). DAPI-stained images are also shown (left). (D) The percentage of TUNEL positive cells relative to DAPI positive cells when cultured in the presence or absence of rPEDF is shown in mean±standard deviation of 3 independent experiments. (E) mRNA expression of Lin28, Oct3/4 and Nanog in 253G1 cell cultured in the presence or absence of rPEDF (50 µg/ml) was measured on day 4 of culture by quantitative RT-PCR. GAPDH was used as the internal standard for calibration of the mRNA expression level. The mRNA expression level of each gene when cultured in the presence of rPEDF is shown in a proportion to the expression level when cultured in the absence of rPEDF. The results of 3 independent experiments are shown in mean and standard deviation (error bar).

FIG. 5-2 shows involvement of p38 MAPK and caspase-3 pathways in the induction of apoptosis for iPSC via PEDF. (F) Phosphorylated p38 MAPK (P-p38) or p38 MAPK (P38) in iPSC(−) after 6 hr of serum depletion treatment, and iPSC 5 min or 15 min after addition of PEDF was detected by Western blotting using a specific antibody. p38 was used as the internal standard (left panel). Phosphorylated p38 MAPK (P-p38) or p38 MAPK (P38) in iPSC(−) after serum depletion treatment, and iPSC 10 min after addition of PEDF and DMSO, or PEDF and p38 inhibitor (SB203580) was detected by Western blotting (right panel). (G) Procaspase-3 and activated caspase-3 in iPSC(−) after serum depletion treatment, and iPSC 5 min or 15 min after addition of PEDF was detected by Western blotting using a specific antibody.

FIG. 6 shows that PEDF induces apoptotic cell death of human ES cell (KhES-1). KhES-1 cells were cultured in the presence of 50 µg/ml rPEDF (lower panel) or absence thereof (upper panel), and apoptotic cell death of KhES-1 cell was examined on day 4 of culture by TUNEL assay and visualized as a green spot. Phase contrast image (left panel), DAPI stained image (middle panel), TUNEL assay image (right panel).

DESCRIPTION OF EMBODIMENTS

Figure 1:
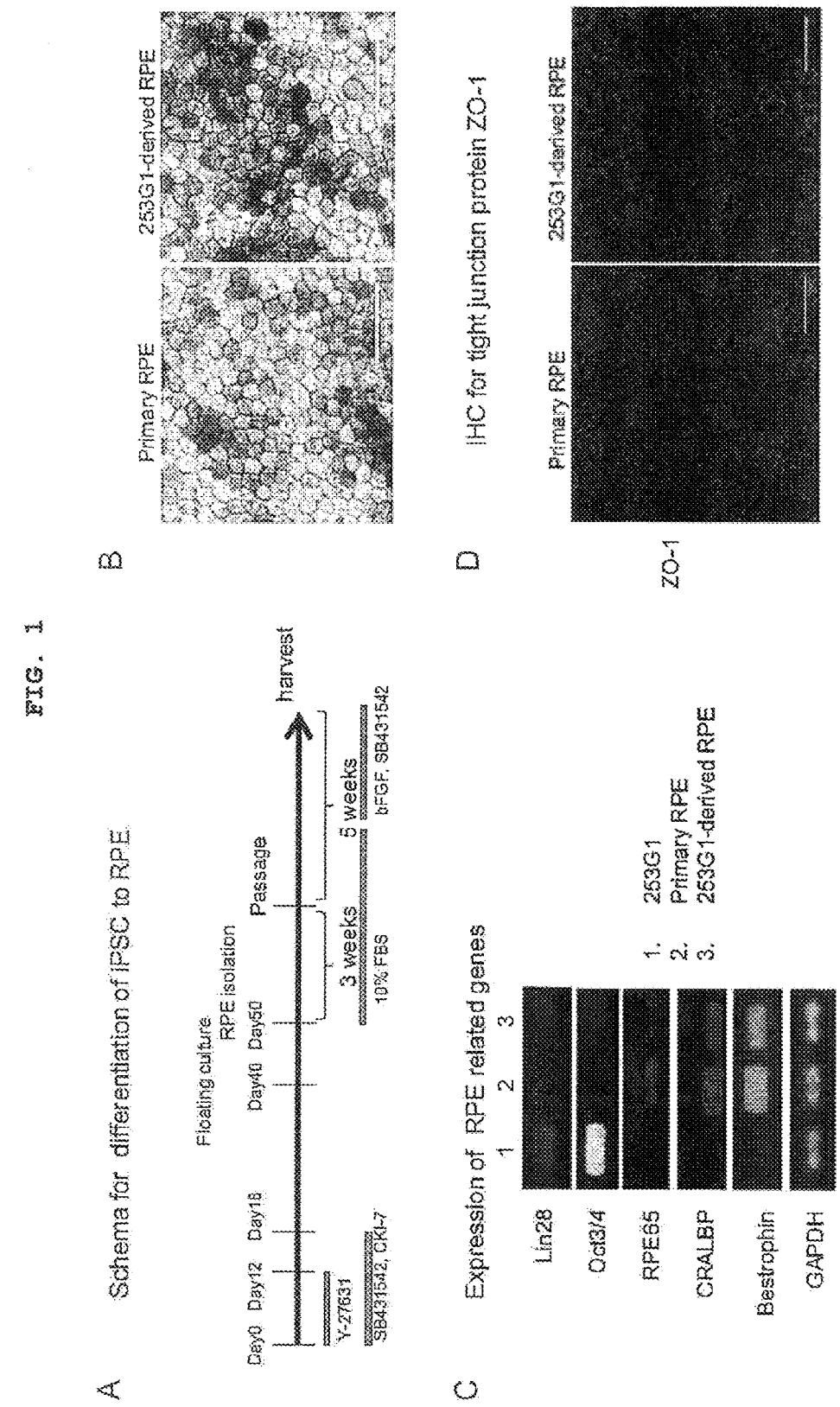
FIG. 1 shows the results of characterization of iPS cell-derived pigment epithelial cell. (A) shows protocol for differentiation of iPS clone into RPE. (B) shows phase contrast images of primary RPE cells (left panel) and iPS clone 253G1-derived RPE cells (right panel). scale bar=50 μm. (C) shows expression of pluripotency-related undifferentiated marker genes (Lin28 and Oct3/4) and RPE cell-specific genes (RPE65, CRALBP and bestrophin) detected by quantitatively RT-PCR. GAPDH was used as the internal standard. (D) shows immunofluorescence staining of tight junction protein ZO-1. The staining was visualized using a secondary antibody Alexa488. scale bar=50 μm.

The present invention provides a method of removing or reducing undifferentiated cells from a differentiated cell population contaminated or having a risk of contamination with undifferentiated cells.

As used herein, the "undifferentiated cell" is not particularly limited as long as it maintains an undifferentiated state (pluripotency or multilineage potential), and has a potential of tumorigenicity (concept including both teratoma formation and canceration in the present invention) after transplantation into living organisms. Typically, it is a cell that, when transplanted, differentiates randomly due to its undifferentiating nature, allowing cell types other than the cell of interest to form a tumor mass; more typically, it is a pluripotent stem cell possessing a "self-renewal ability" that enables it to proliferate while retaining the undifferentiated state, and "pluripotency" that enables it to differentiate into all the three germ layer lineages. Pluripotent stem cell is characterized by expression of one or more undifferentiated markers, for example, positive alkaline phosphatase staining, positive SSEA3 staining, positive SSEA4 staining, positive Tra-1-60 staining, positive Tra-1-81 staining, gene expression of Lin28, Oct3/4, Nanog, Sox2, Cripto, Dax1, ERas, Fgf4, Esg1, Rex1, Zfp296, UTF1, GDF3, Sa114, Tbx3, Tcf3, DNMT3L, DNMT3B, expression of miR-290 cluster miRNA, miR-302 cluster miRNA and the like. More specifically, the undifferentiated cell in the present invention is, for example, a pluripotent stem cell expressing at least one undifferentiated marker from Lin28, Oct3/4 and Nanog. Examples of such pluripotent stem cell include induced pluripotent stem cell (iPS cell), embryonic stem cell (ES cell), multipotent adult progenitor cell (MAPC) isolated from bone marrow mesenchymal cells, Muse cells isolated from bone marrow mesenchymal cells and the like, embryonic germ (EG) cell derived from a primordial germ cell, multipotent germline stem (mGS) cell isolated in the process of establishment and culture of GS cell from testis tissue and the like. The ES cell may be ntES cell produced from a somatic cell by nuclear reprogramming. Preferred are iPS cells or ES cells.

The undifferentiated cell in the present invention also encompasses a cell having multilineage potential which, when the above-mentioned pluripotent stem cell is induced to differentiate, loses pluripotency but does not differentiate into the differentiated cell of interest, maintains an undifferentiated state, and has a tumorigenic potential.

The "differentiated cell population" is a cell population comprising differentiated cell as a main component cell. The "differentiated cell" as used herein refers to any cell free of infinite proliferative capacity, and free of an ability to differentiate beyond a germ layer. Examples thereof include, but are not limited to, terminally differentiated cells such as skin cell, eye cell, brain cell, hair cell, mouth cavity mucous to membrane, lung cell, hepatocyte, stomach mucosal cell, gut cell, splenocyte, pancreatic cell, kidney cell, blood cell (e.g., peripheral blood mononuclear cells (including T cell and non-T cell), peripheral blood lymphocyte, cord blood cell and the like), epithelial cell, endothelial cell, myocyte (cardiac is muscle cell and the like), chondrocyte, fibroblast and the like, tissue stem cell having multilineage potential (multipotency) and limitative self-renewal ability such as neural stem cell, hematopoietic stem cell, mesenchymal stem cell derived from wisdom tooth and the like, and the like, monopotent tissue progenitor cell such as spermatogonial stem cell, muscle stem cell and the like, and the like. In addition, primary cultured cell, passage cell and the like of these are also encompassed. While tissue stem cells may have multilineage potential, it is needless to say that a tissue stem cell which is mixed in normal differentiated cells in the body, and confirmed to have no or extremely low tumorigenicity risk as a transplantation material for conventional cell transplantation therapy is classified as the "differentiated cell" in light of the gist of the present invention. In light of the object of the present invention, moreover, a dedifferentiated cancer cell is not included in the "differentiated cell" in the present invention.

The method of removing or reducing undifferentiated cells of the present invention is characterized in that PEDF is contacted with a differentiated cell population contaminated or having a risk of contamination with undifferentiated cells. As a result, undifferentiated cells can be removed or reduced from a differentiated cell population.

The mechanism of removing or reducing undifferentiated cells by contacting PEDF is not particularly limited, and includes inhibition of growth of undifferentiated cells by PEDF, induction of apoptosis of undifferentiated cell and the like. A preferable mechanism is, for example, induction of apoptosis of undifferentiated cells. Utilizing the effect of PEDF to induce apoptosis of undifferentiated cells, undifferentiated cells can be removed or reduced from a differentiated cell population contaminated or having a risk of contamination with undifferentiated cells, and the differentiated cells can be purified.

A differentiated cell that can be induced by PEDF to undergo apoptosis is not preferable as a target cell in the present invention. For example, since PEDF is already known to induce apoptosis of vascular endothelial cell among the differentiated cells, the differentiated cell to be the target in the present invention is preferably a differentiated cell other than vascular endothelial cell. Since PEDF may induce cell death of corneal epithelial cells, the differentiated cell to be the target in the present invention is preferably a cell other than corneal epithelial cells. However, it is also possible to induce apoptosis specifically in an undifferentiated cell by controlling the concentration of PEDF based on the difference in the sensitivity to PEDF between undifferentiated cell and differentiated cell. Therefore, the present invention does not eliminate application to a PEDF-sensitive differentiated cell as long as it has lower sensitivity than undifferentiated cells.

While the differentiated cell population contaminated or having a risk of contamination with undifferentiated cells is not particularly limited, it is typically a differentiated cell population obtained by inducing differentiation of any of the above-mentioned undifferentiated cells, preferably pluripotent stem cell. The differentiated cell population is prepared by the steps of (1) producing a pluripotent stem cell, and (2) inducing differentiation of the obtained undifferentiated cell and, in many cases, particularly for administration to the living body, a cell purification step is necessary to reduce the tumor risk. The present invention can be an extremely convenient and useful technique for the cell purification step.

(1) Production Method of Pluripotent Stem Cell (a) iPS Cell iPS cell is an artificial stem cell derived from a somatic cell, which can be produced by introducing a specific reprogramming factor in the form of a DNA or protein into a somatic cell, and show almost equivalent property (e.g., pluripotent differentiation and proliferation potency based on self-renewal) as ES cells (K. Takahashi and S. Yamanaka (2006) Cell, 126:663-676; K. Takahashi et al. (2007), Cell, 131:861-872; J. Yu et al. (2007), Science, 318:1917-1920; Nakagawa, M. et al., Nat. Biotechnol. 26:101-106 (2008); WO2007/069666). The reprogramming factor may be constituted with a gene specifically expressed by ES cell, a gene product or non-coding RNA thereof, a gene playing an important role for the maintenance of undifferentiation of ES cell, a gene product or non-coding RNA thereof, or a low molecular weight compound. Examples of the gene contained in the reprogramming factor include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, Glis1 and the like. These reprogramming factors may be used alone or in combination. Examples of the combination of the reprogramming factors include combinations described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO2010/111409, WO2010/111422, WO2010/115050, WO2010/124290, WO2010/147395, WO2010/147612, Huangfu D, et al. (2008), Nat. Biotechnol., 26: 795-797, Shi Y, et al. (2008), Cell Stem Cell, 2: 525-528, Eminli S, et al. (2008), Stem Cells. 26:2467-2474, Huangfu D, et al. (2008), Nat. Biotechnol. 26:1269-1275, Shi Y, et al. (2008), Cell Stem Cell, 3, 568-574, Zhao Y, et al. (2008), Cell Stem Cell, 3:475-479, Marson A, (2008), Cell Stem Cell, 3, 132-135, Feng B, et al. (2009), Nat Cell Biol. 11:197-203, R. L. Judson et al., (2009), Nat. Biotech., 27:459-461, Lyssiotis C A, et al. (2009), Proc Natl Acad Sci USA. 106:8912-8917, Kim J B, et al. (2009), Nature. 461:649-643, Ichida J K, et al. (2009), Cell Stem Cell. 5:491-503, Heng J C, et al. (2010), Cell Stem Cell. 6:167-74, Han J, et al. (2010), Nature. 463:1096-100, Mali P, et al. (2010), Stem Cells. 28:713-720, and Maekawa M, et al. (2011), Nature. 474:225-9.

Examples of the above-mentioned reprogramming factor include factors used for enhancing the establishment efficiency, such as histone deacetylase (HDAC) inhibitors [e.g., low-molecular inhibitors such as valproic acid (VPA), trichostatin A, sodium butyrate, MC 1293, and M344, nucleic acid-based expression inhibitors such as siRNAs and shRNAs against HDAC (e.g., HDAC1 siRNA Smartpool® (Millipore), HuSH 29mer shRNA Constructs against HDAC1 (OriGene) and the like), and the like], MEK inhibitor (e.g., PD184352, PD98059, U0126, SL327 and PD0325901), Glycogen synthase kinase-3 inhibitor (e.g., Bio and CHIR99021), DNA methyl transferase inhibitors (e.g., 5-azacytidine), histone methyl transferase inhibitors [for example, low-molecular inhibitors such as BIX-01294, and nucleic acid-based expression inhibitors such as siRNAs and shRNAs against Suv39h1, SctDB1 SetDB1 and G9a], L-channel calcium agonist (e.g., Bayk8644), butyric acid, TGFβ inhibitor or ALK5 inhibitor (e.g., LY364947, SB431542, 616453 and A-83-01), p53 inhibitor (e.g., siRNA and shRNA against p53), ARID3A inhibitor (e.g., siRNA and shRNA against ARID3A), miRNA such as miR-291-3p, miR-294, miR-295, mir-302 and the like, Wnt Signaling (e.g., soluble Wnt3a), neuropeptide Y, prostaglandins (e.g., prostaglandin E2 and prostaglandin J2), hTERT, SV40LT, UTF1, IRX6, GLIS1, PITX2, DMRTB1 and the like. In the present specification, these factors used for enhancing the establishment efficiency are not particularly distinguished from the reprogramming factor.

When the reprogramming factor is in the form of a protein, it may be introduced into a somatic cell by a method, for example, lipofection, fusion with cell penetrating peptide (e.g., TAT derived from HIV and polyarginine), microinjection and the like.

When the reprogramming factor is in the form of a DNA, it may be introduced into a somatic cell by the method using, for example, vector of virus, plasmid, artificial chromosome and the like, lipofection, liposome, microinjection and the like. Examples of the virus vector include retrovirus vector, lentivirus vector (Cell, 126, pp. 663-676, 2006; Cell, 131, pp. 861-872, 2007; Science, 318, pp. 1917-1920, 2007), adenovirus vector (Science, 322, 945-949, 2008), adeno-associated virus vector, Sendai virus vector (WO 2010/008054) and the like. Examples of the artificial chromosome vector include human artificial chromosome (HAC), yeast artificial chromosome (YAC), bacterial artificial chromosome (BAC, PAC) and the like. As the plasmid, plasmids for mammalian cells can be used (Science, 322:949-953, 2008). The vector can contain regulatory sequences of promoter, enhancer, ribosome binding sequence, terminator, polyadenylation site and the like so that a nuclear reprogramming substance can be expressed and further, where necessary, a selection marker sequence of a drug resistance gene (e.g., kanamycin resistance gene, ampicillin resistance gene, puromycin resistance gene and the like), thymidine kinase gene, diphtheria toxin gene and the like, a reporter gene sequence of green fluorescent protein (GFP), β glucuronidase (GUS), FLAG and the like, and the like. Moreover, to cut out a gene encoding a reprogramming factor or both a promoter and gene encoding a reprogramming factor bound to the promoter after introduction into a somatic cell, the above-mentioned vector may have a LoxP sequence before and after thereof.

When in the form of RNA, for example, it may be introduced into a somatic cell by means of lipofection, microinjection and the like, and RNA incorporating 5-methylcytidine and pseudouridine (TriLink Biotechnologies) may be used to suppress degradation (Warren L, (2010) Cell Stem Cell. 7:618-630).

Examples of the culture medium for inducing iPS cell include 10-15% FBS-containing DMEM, DMEM/F12 or DME culture medium (these culture media can further contain LIF, penicillin/streptomycin, puromycin, L-glutamine, nonessential amino acids, β-mercaptoethanol and the like as appropriate) or a commercially available culture medium [for example, culture medium for mouse ES cell culture (TX-WES culture medium, Thromb-X), culture medium for primate ES cell (culture medium for primate ES/iPS cell, Reprocell), serum-free medium (mTeSR, Stemcell Technologies)] and the like.

Examples of the culture method include contacting a somatic cell with a reprogramming factor on 10% FBS-containing DMEM or DMEM/F12 culture medium at 37° C. in the presence of 5% $CO_2$ and culturing the cell for about 4-7 days, thereafter reseeding the cells on feeder cells (e.g., mitomycin C-treated STO cells, SNL cells etc.), and culturing the cells in a bFGF-containing culture medium for primate ES cell from about 10 days after the contact of the somatic cell and the reprogramming factor, whereby iPS-like colonies can be obtained after about 30-about 45 days or longer from the contact.

Alternatively, the cells are cultured on feeder cells (e.g., mitomycin C-treated STO cells, SNL cells etc.) at 37° C. in the presence of 5% $CO_2$ in a 10% FBS-containing DMEM culture medium (which can further contain LIF, penicillin/streptomycin, puromycin, L-glutamine, nonessential amino acids, β-mercaptoethanol and the like as appropriate), whereby ES-like colonies can be obtained after about 25-about 30 days or longer. Desirably, a method using a somatic cell itself to be reprogrammed, or an extracellular matrix (e.g., Laminin-5 (WO 2009/123349) and Matrigel (BD)), instead of the feeder cells (Takahashi K, et al. (2009), PLoS One. 4:e8067 or WO 2010/137746), can be mentioned.

Besides the above, a culture method using a serum-free medium can also be recited as an example (Sun N, et al. (2009), Proc Natl Acad Sci USA. 106:15720-15725). Furthermore, to enhance establishment efficiency, an iPS cell may be established under hypoxic conditions (oxygen concentration of not less than 0.1% and not more than 15%) (Yoshida Y, et al. (2009), Cell Stem Cell. 5:237-241 or WO2010/013845).

The culture medium is exchanged with a fresh culture medium once a day during the above-mentioned cultures, from day 2 from the start of the culture. While the cell number of the somatic cells used for nuclear reprogramming is not limited, it is about $5 \times 10^3$-about $5 \times 10^6$ cells per 100 $cm^2$ in a culture dish.

The iPS cell can be selected based on the shape of the formed colony. When a drug resistance gene which is expressed in association with a gene (e.g., Oct3/4, Nanog) expressed when a somatic cell is reprogrammed is introduced as a marker gene, an established iPS cell can be selected by culturing in a culture medium (selection culture medium) containing a corresponding drug. When the marker gene is a fluorescent protein gene, iPS cell can be selected by observation with a fluorescence microscope, when it is a luminescence enzyme gene, iPS cell can be selected by adding a luminogenic substrate, and when it is a chromogenic enzyme gene, iPS cell can be selected by adding a chromogenic substrate.

The term "somatic cell" used in the present specification means any animal cell (preferably, cells of mammals inclusive of human) excluding germ line cells and totipotent cells such as ovum, oocyte, ES cells and the like. Somatic cell unlimitatively encompasses any of somatic cells of fetuses, somatic cells of neonates, and mature healthy or pathogenic somatic cells, and any of primary cultured cells, passage cells, and established lines of cells. Specific examples of the somatic cell include (1) tissue stem cells (somatic stem cells) such as neural stem cell, hematopoietic stem cell, mesenchymal stem cell, dental pulp stem cell and the like, (2) tissue progenitor cell, (3) differentiated cells such as lymphocyte, epithelial cell, endothelial cell, myocyte, fibroblast (skin cells etc.), hair cell, hepatocyte, gastric mucosal cell, enterocyte, splenocyte, pancreatic cell (pancreatic exocrine cell etc.), brain cell, lung cell, renal cell and adipocyte and the like, and the like.

When iPS cell is used as a material for cells for transplantation, a somatic cell having the same or substantially the same HLA genotype as the individual receiving the transplantation is desirably used since rejection does not occur. Being "substantially the same" here means that the HLA genotype is the same to the extent the immune reaction against the transplanted cell can be suppressed by an immunosuppressant. For example, it is a somatic cell having an HLA type showing a match of 3 gene loci of HLA-A, HLA-B and HLA-DR or 4 gene loci additionally with HLA-C.

(b) ES Cell

ES cell is a stem cell having pluripotency and proliferation potency based on self-renewal, which is established from an inner cell mass of an early-stage embryo (e.g., blastocyst) of a mammal such as human, mouse and the like.

ES cell is an embryo-derived stem cell derived from an inner cell mass of blastocyst, which is an embryo after morula at 8-cell stage of a fertilized egg, and has an ability to differentiate into any cell constituting an adult body, i.e., pluripotent differentiation potency, and proliferation potency based on self-renewal. The ES cell was discovered in mouse in 1981 (M. J. Evans and M. H. Kaufman (1981), Nature 292:154-156) and thereafter ES cell lines were also established in primates such as human, monkey and the like (J. A. Thomson et al. (1998), Science 282:1145-1147; J. A. Thomson et al. (1995), Proc. Natl. Acad. Sci. USA, 92: 7844-7848; J. A. Thomson et al. (1996), Biol. Reprod., 55: 254-259; J. A. Thomson and V. S. Marshall (1998), Curr. Top. Dev. Biol., 38:133-165).

ES cell can be established by removing an inner cell mass from the blastocyst of a fertilized egg of a target animal, and culturing the inner cell mass on fibroblast feeder cells. In addition, the cells can be maintained by passage culture using a culture medium added with substances such as leukemia inhibitory factor (LIF), basic fibroblast growth factor (bFGF) and the like. The methods of establishment and maintenance of human and monkey ES cells are described in, for example, U.S. Pat. No. 5,843,780; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; H. Kawasaki et al. (2002), Proc. Natl. Acad. Sci. USA, 99:1580-1585; Klimanskaya I, et al. (2006), Nature. 444:481-485 and the like.

Using, as a culture medium for preparing ES cells, for example, a DMEM/F-12 culture medium supplemented with 0.1 mM 2-mercaptoethanol, 0.1 mM nonessential amino acids, 2 mM L-glutamic acid, 20% KSR and 4 ng/ml bFGF, human ES cells can be maintained under wet atmosphere at 37° C., 2% $CO_2$/98% air (O. Fumitaka et al. (2008), Nat. Biotechnol., 26:215-224). In addition, ES cells require passage every 3-4 days, and the passage in this case can be performed using, for example, 0.25% trypsin and 0.1 mg/ml collagenase IV in PBS containing 1 mM $CaCl_2$ and 20% KSR.

ES cells can be generally selected by the Real-Time PCR method using the expression of a gene marker such as alkaline phosphatase, Oct-3/4, Nanog and the like as an index. Particularly, for selection of human ES cell, expression of a gene marker such as OCT-3/4, NANOG, ECAD and the like can be used as an index (E. Kroon et al. (2008), Nat. Biotechnol., 26:443-452).

As for human ES cell line, for example, WA01 (H1) and WA09 (H9) are available from WiCell Research Institute, and KhES-1, KhES-2 and KhES-3 are available from Institute for Frontier Medical Sciences, Kyoto University (Kyoto, Japan).

(c) Other Pluripotent Stem Cell

EG cell is a cell having pluripotency similar to that of ES cells, which is established from a primordial germ cell at the prenatal period. It can be established by culturing a primordial germ cell in the presence of a substance such as LIF, bFGF, a stem cell factor and the like (Y. Matsui et al. (1992), Cell, 70:841-847; J. L. Resnick et al. (1992), Nature, 359: 550-551).

(D) Induced Pluripotent Stem Cell nt ES cell is an ES cell derived from a cloned embryo prepared by a nuclear transplantation technique, and has almost the same property as the ES cell derived from a fertilized egg (T. Wakayama et al. (2001), Science, 292:740-743; S. Wakayama et al. (2005), Biol. Reprod., 72:932-936; J. Byrne et al. (2007), Nature, 450:497-502). That is, an ES cell established from an inner cell mass of a blastocyst derived from a cloned embryo obtained by substituting the nucleus of an unfertilized egg with the nucleus of a somatic cell is an nt ES (nuclear transfer ES) cell. For production of an nt ES cell, a combination of the nuclear transplantation technique (J. B. Cibelli et al. (1998), Nature Biotechnol., 16:642-646) and the ES cell production technique (mentioned above) is used (Kiyoka Wakayama et al., (2008), Experimental Medicine, Vol. 26, No. 5 (Suppl.), pp. 47-52). In nuclear transplantation, reprogramming can be performed by injecting the nucleus of a somatic cell to an enucleated unfertilized egg of a mammal, and culturing for a few hours.

Muse cell is a pluripotent stem cell produced by the method described in WO2011/007900. In more detail, it is a cell having pluripotency, which is obtained by subjecting a fibroblast or a bone marrow stromal cell to a trypsin treatment for a long time, preferably 8 hr or 16 hr, and thereafter culturing the cells in a suspended state, and positive for SSEA-3 and CD105.

mGS cell can be produced from a testis cell according to the method described in WO 2005/100548.

MAPC can be isolated from bone marrow according to the method described in J. Clin. Invest. 109:337-346 (2002).

(2) Induction of Differentiation from Pluripotent Stem Cell into Various Differentiated Cells Induction of differentiation from a stem cell into various differentiated cells can be performed by any method known per se. For example, the cells can be differentiated into hematopoietic progenitor cells by co-culture with C3H10T1/2 cell line, obtained by irradiating human ES cells, to induce a saccular structure (ES-sac) (Blood, 111: 5298-306, 2008). As a method for differentiation induction of ES cells into neural stem cell, nerve cell, various methods such as embryoid formation method (Mech Div 59(1) 89-102, 1996), retinoic acid method (Dev Biol 168(2) 342-57, 1995), SDIA method (Neuron 28(1) 31-40, 2000), NSS method (Neurosci Res 46(2) 241-9, 2003) and the like are known. As a method of inducing ES cell into cardiomyocyte, a method of adding factors such as retinoic acid, TGFβ1, FGF, dynorphin B, ascorbic acid, nitric oxide, FGF2 and BMP2, Wnt11, PP2, Wnt3a/Wnt inhibitor and the like to a medium, the cardiac muscle differentiation induction method of Noggin (Nat Biotechnol 23(5) 611, 2005) and the like have been reported heretofore. Furthermore, a differentiation induction method of ES/iPS cells into retinal cells by the SDIA method (Proc Natl Acad Sci USA 99 1580-5, 2002) and SFEB method (Nat Neurosci 8 288-96, 2005) and the like are known. The former includes co-culture of cell clusters of finely-divided ES cell colony with mouse stroma-derived PA6 cells, and the latter is a method including addition of Dkk1/Lefty-A when embryoid is formed by floating culture in a serum-free medium, in an attempt to enhance differentiation induction efficiency of the cells in the forebrain region including retinal progenitor cells. Further adhesion culture thereof can induce mature RPE cells and visual cells (Proc Natl Acad Sci USA 102 11331-6, 2005; Nat Biotechnol 26 215-24, 2008).

In addition, differentiation induction methods from tissue stem cells into somatic cells such as differentiation induction method from hematopoietic stem cell into various hematopoietic cells, differentiation induction method from vascular endothelial progenitor cell into blood vessel cell, differentiation induction method from neural stem cell into various nerve cells, differentiation induction method from mesenchymal stem cell into adipocyte, myotube cell and the like, and the like are also well known in the technical field.

The method of removing or reducing undifferentiated cells in the present invention is characterized by contact of a pigment epithelium-derived factor (PEDF) with a differentiated cell population contaminated or having a risk of contamination with undifferentiated cells to induce apoptosis of undifferentiated cells.

The methods of contacting PEDF with a differentiated cell population are largely divided into (A) a culture method including addition of PEDF to the medium of a differentiated cell population, (B) a method including co-culture of a differentiated cell population with a PEDF-secreting cell, and (C) a method including secretion production of PEDF in a differentiated cell.

(A) Culture Method with Addition of PEDF to Medium for Differentiated Cell Population Examples of PEDF to be added to the medium include, in the amino acid sequence shown by SEQ ID NO: 2, human PEDF that consists of the amino acid sequence shown by amino acid Nos. 1-399 (RefSeq Accession No. NP#002606), orthologs thereof in other mammals (e.g., mouse PEDF (RefSeq Accession No. NP#035470), rat PEDF (RefSeq Accession No. NP#808788), bovine PEDF (RefSeq Accession No. NP#776565), canine PEDF (RefSeq Accession No. XP#854014), chimpanzee PEDF (RefSeq Accession No. XP#001155004), chicken PEDF (RefSeq Accession No. XP#001234865) etc.), natural allelic variants thereof and polymorphic variants thereof (e.g., variant wherein amino acid No. 53 (Thr) in SEQ ID NO: 2 is substituted by Met, variant wherein amino acid No. 113 (Pro) in SEQ ID NO: 2 is substituted by Arg etc.), splicing variant (e.g., Journal of Neuroscience 15(7): 4992-5003, 1995; Protein Expression and Purification 6(4): 447-456, 1995; Investigative Ophthalmology and Visual Science 43(3): 821-829, 2002), natural and artificial active variants and the like. It is desirable to use PEDF allogeneic to the animal species from which the differentiated cell to be the target in the method of the present invention is derived; however, xenogeneic PEDF can also be used.

PEDF may be isolated and purified from a cell that produces said protein, such as RPE cell, adipocyte, hepatocyte, dendritic cell and the like of warm-blooded animals, or may also be chemically synthesized or biochemically synthesized in a cell-free translation system. Alternatively, it may be a recombinant protein produced from a transformant incorporating a nucleic acid comprising a base sequence that encodes the above-described amino acid sequence.

When natural PEDF secreted from RPE cell, adipocyte, hepatocyte, dendritic cell and the like, preferably RPE cell, of a warm-blooded animal is used, for example, PEDF producing cells obtained by differentiation induction of primary cultured cells and pluripotent stem cells are cultured in a suitable medium, the culture supernatant is separated by filtration, centrifugation and the like, and the supernatant (conditioned medium) may be directly used. Alternatively, PEDF may be used after isolation and purification or partial purification by subjecting the supernatant to chromatography such as reversed-phase chromatography, ion exchange chromatography, affinity chromatography and the like, and the like.

As a medium for PEDF producing cells, a basal medium generally used for culturing animal cells, which is added with 1-20% of serum or serum replacement, is used. Examples of the basal medium include GMEM (Glasgow Minimum Essential Medium), IMDM (Iscove's Modified Dulbecco's Medium), Medium 199, Eagle's Minimum Essential Medium (EMEM), aMEM, Dulbecco's modified Eagle's Medium (DMEM), Ham's F12 medium, RPMI 1640 medium, Fischer's medium, and a combined medium thereof and the like. Examples of the serum replacement include albumin, transferrin, fatty acid, insulin, collagen precursor, trace element, Knockout Serum Replacement (KSR), ITS-supplement and mixtures thereof and the like. PEDF producing cells can be cultured, in the case of RPE, for example, at 30-40° C., preferably 37-38.5° C., for 6-144 hr, preferably 24-42 hr, under 1-10%, preferably 2-100, $CO_2$ atmosphere.

When natural PEDF is used as a PEDF source, it can be added to a medium for differentiated cell population such that the final concentration of PEDF is 0.01-100 µg/ml, irrespective of whether the source is conditioned medium, purified or partially purified PEDF.

When recombinant protein (rPEDF) is used as a PEDF source, a transformant containing a nucleic acid encoding PEDF is cultured in a suitable medium, the culture supernatant is separated by filtration, centrifugation and the like, and the supernatant (conditioned medium) may be used directly, or the supernatant may be subjected to chromatography and the like similar to those mentioned above, and rPEDF is isolated and purified or partially purified and used.

The nucleic acid encoding PEDF may be DNA or RNA, or DNA/RNA chimera, preferably DNA. Additionally, the nucleic acid may be double-stranded or single-stranded. In the case of a double-stranded nucleic acid, it may be a double-stranded DNA, a double-stranded RNA, or a DNA:RNA hybrid. In the case of a single strand, it may be a sense strand (that is, coding strand), or an antisense strand (that is, non-coding strand). Examples of the DNA encoding PEDF include human pre-PEDF (RefSeq Accession No. NM#002615) composed of the base sequence shown by SEQ ID NO: 1, orthologs in other mammals (e.g., mouse PEDF (RefSeq Accession No. NM#011340), rat PEDF (RefSeq Accession No. NM#177927), bovine PEDF (RefSeq Accession No. NM#174140), canine PEDF (RefSeq Accession No. XM#848921), chimpanzee PEDF (RefSeq Accession No. XM#001155004), chicken PEDF (RefSeq Accession No. XM#001234864) etc.), in addition, natural allelic variants thereof and polymorphic variants thereof (e.g., variant wherein amino acid No. 53 (Thr) in SEQ ID NO: 2 is substituted by Met, variant wherein amino acid No. 113 (Pro) in SEQ ID NO: 2 is substituted by Arg etc.), splicing variant (e.g., Journal of Neuroscience 15(7): 4992-5003, 1995; Protein Expression and Purification 6(4): 447-456, 1995; Investigative Ophthalmology and Visual Science 43(3): 821-829, 2002), DNA encoding natural and artificial active variants and to the like.

As DNA encoding PEDF, for example, cDNA can be isolated by synthesizing a suitable primer based on the sequence information of the DNA, and performing RT-PCR using RNA is collected from the above-mentioned PEDF producing cell, preferably RPE cell, as a template. Alternatively, genomic DNA of PEDF can also be isolated by preparing genomic DNA of a warm-blooded animal according to a conventional method, and using genomic PCR and the like. PEDF is known to include many splicing variants, and apoptosis induction activity on undifferentiated cells may vary depending on the species of the variant. Thus, use of genomic DNA may sometimes be advantageous.

The isolated DNA is cloned into an expression vector suitable for the host cell, and the vector is introduced into the host cell according to a conventional method, whereby a transformant can be produced. The host cell is not particularly limited, and bacteria such as *Escherichia coli, Bacillus subtilis* and the like, yeast, insect cell, animal cell and the like can be used. Natural PEDF undergoes post-translational modification such as O-glycosylation and N-glycosylation, phosphorylation and the like, which may affect the apoptosis induction activity of PEDF in undifferentiated cells. Thus, preferably an animal cell, particularly an animal cell allogeneic to the animal from which DNA encoding PEDF is derived can be used. As the animal cell, for example, monkey COS-7 cell, monkey Vero cell, Chinese hamster ovary cell (CHO cell), dhfr gene-deficient CHO cell, mouse L cell, mouse AtT-20 cell, mouse myeloma cell, rat GH3 cell, human FL cell, HEK293 cell and the like are used. Transformant can be cultured by a method known per se which is appropriately selected according to the type of the host cell. rPEDF can be isolated by subjecting the culture supernatant of the transformant to chromatography and the like in the same manner as above. The supernatant may be directly added to a medium for differentiated cell population.

When rPEDF is used as a PEDF source, it can be added to a medium for differentiated cell population such that the final concentration of rPEDF is 0.1-500 µg/ml, irrespective of whether the source is conditioned medium, purified or partially purified rPEDF.

(B) Method of Co-Culturing Differentiated Cell Population and PEDF-Secreting Cell Examples of the PEDF-secreting cell include primary culture of the above-mentioned RPE cell, adipocyte, hepatocyte, dendritic cell and the like, preferably RPE cell, of a warm-blooded animal, or RPE cell, adipocyte, hepatocyte, dendritic cell etc. induced to differentiate from pluripotent stem cells such as iPS cell and the like, preferably RPE cell. While a method of co-culturing differentiated cell population and PEDF-secreting cell is not particularly limited, preferably, as described in the below-mentioned Examples, a culture method using a transwell plate wherein PEDF-secreting cells are seeded in a culture dish coated with a suitable coating agent, and a differentiated cell population is seeded in a culture insert can be mentioned. A large amount of differentiated cell population can also be treated by scaling up based on a similar principle. Culture can be performed, for example, at 30-40° C., preferably 37-38.5° C., for 6-144 hr, preferably 24-42 hr, under 1-10%, preferably 2-10%, $CO_2$ atmosphere.

(C) Method of Producing PEDF by Secretion by Differentiated Cell Itself

When differentiated cell is RPE cell, adipocyte, hepatocyte, dendritic cell etc., preferably RPE cell, induced to differentiate from pluripotent stem cells, apoptosis of undifferentiated cell contaminating a differentiated cell population can be induced by the action of PEDF secreted by the differentiated cell itself, without adding PEDF to the medium or co-culture with PEDF-secreting cell.

Alternatively, an expression vector for animal cells, which contains DNA encoding PEDF in the above-mentioned (A), is introduced into pluripotent stem cells such as iPS cell and the like, and expression of rPEDF is induced during or after induction of differentiation of the pluripotent stem cells to cause suicide of the remaining undifferentiated cells, or apoptosis of the undifferentiated cells can also be induced by the trans-effect of rPEDF secreted from the differentiated cells. Examples of the method of inducing expression of rPEDF in the remaining undifferentiated cells include a method using an expression vector having an inducible promoter such as a metallothionein-1 gene promoter (heavy metals such as gold, zinc, cadmium and the like, steroids such as dexamethasone and the like, alkylating agent, chelating agent, cytokine and the like induce expression) and the like, a method including designing a vector such that a DNA encoding PEDF is functionally linked to a promoter when Cre recombinase is activated using the Cre-loxP system (e.g., a promoter and a DNA encoding PEDF are separated by two loxP sequences arranged in the same direction. An expression cassette of selection marker gene such as drug resistance gene and the like is preferably inserted between the two loxP sequences) and the like. On the other hand, the method for inducing apoptosis of undifferentiated cells by the trans-effect of rPEDF secreted by differentiated cells includes, in addition to a method similar to the above-mentioned method, a method using an expression vector having a differentiated cell-specific promoter. Examples of the differentiated cell-specific promoter include an endogenous promoter of PEDF, which is specific to RPE and the like, a promoter of albumin and α-fetoprotein, which is specific to the liver and the like, a promoter of prostate-specific antigen (PSA), which is specific to prostate, a promoter of mitochondrial creatin kinase (MCK), which is specific to various organs such as muscle, brain and the like, promoters of myelin basic protein (MB), glial fiber acidic protein (GFAP) and neuron-specific enolase (NSE), which are specific to nerve system of brain and the like, and the like.

The differentiated cell population obtained by contacting a pigment epithelium-derived factor (PEDF) with a differentiated cell population contaminated or having a risk of contamination with undifferentiated cells to induce apoptosis of undifferentiated cells as mentioned above can be purified to be substantially free of an undifferentiated cell. As used herein, "substantially free of an undifferentiated cell" means that when a differentiated cell population is transplanted to a recipient in an amount corresponding to transplantation, the undifferentiated cells have been reduced and removed to a level not causing a tumor. Being "substantially free of an undifferentiated cell" can be verified by, for example, culturing the differentiated cell population again under undifferentiating conditions and detecting development of an undifferentiated cell by utilizing properties specific to the undifferentiated cells. Examples of the specific property include colony formation, expression of undifferentiation specific antigen, expression of undifferentiation specific gene and the like. While the undifferentiation specific antigen is not limited, it is selected from the group consisting of SSEA-1, SSEA-3, SSEA-4, Tra1-60 and Tra1-81. In human, SSEA-1 is not detected in undifferentiated cells. Therefore, SSEA-3, SSEA-4, Tra1-60 and Tra1-81 are preferably used instead of SSEA-1. Examples of the undifferentiation specific gene include the genes recited in WO 2007/069666.

It is preferable to detect development of undifferentiated cells by observing colony formation since it is convenient and can provide sufficient sensitivity and specificity. While measurement of colony is not particularly limited, for example, colonies are counted under a microscope and evaluated by the number thereof. The measurement may be mechanically performed or performed by visual observation. On the other hand, cells showing expression of an undifferentiation specific antigen or gene can be evaluated based on the number of cells expressing such antigen or gene by using FACS.

A differentiated cell population substantially free of undifferentiated cells is produced as a parenteral preparation such as injection, suspension, drip infusion and the like, by mixing same with a pharmaceutically acceptable carrier according to a conventional means. Examples of the pharmaceutically acceptable carrier that can be contained in the parenteral preparation include aqueous solutions for injection such as physiological saline, isotonic solution containing glucose, other auxiliary agents (e.g., D-sorbitol, D-mannitol, sodium chloride and the like) and the like. The agent for transplantation therapy of the present invention may be mixed with, for example, buffering agent (e.g., phosphate buffer, sodium acetate buffer), soothing agent (e.g., benzalkonium chloride, procaine hydrochloride and the like), stabilizer (e.g., human serum albumin, polyethylene glycol and the like), preservative, antioxidant and the like. When the agent for transplantation therapy of the present invention is formulated as an aqueous suspension, the differentiated cells may be suspended in the above-mentioned aqueous solution at about $1 \times 10^6$-about $1 \times 10^8$ cells/mL.

The agent for transplantation therapy of the present invention can also be provided in a state of cryopreservation under the conditions generally used for cryopreservation of cells, and used by melting when in use. In this case, it may further contain a serum or serum replacement, an organic solvent (e.g., DMSO) and the like. In this case, the concentration of the serum or a serum replacement is not particularly limited, and can be about 1-about 30% (v/v), preferably about 5-about 20% (v/v). The concentration of the organic solvent is not particularly limited and can be 0-about 50% (v/v), preferably about 5-about 20% (v/v).

The present invention also provides an agent for inducing apoptosis of undifferentiated cells, which contains PEDF. As used herein, PEDF may be, as described in the above-mentioned (A) and (B), a culture supernatant (conditioned medium) of a cell that produces natural or recombinant PEDF by secretion, a completely or partially purified product from the supernatant, or a cell itself that produces natural or recombinant PEDF by secretion.

In addition to the above-mentioned use in vitro, the agent for inducing apoptosis of the present invention can also be used as an inhibitor of tumor formation in vivo, by concurrent administration or transplantation during transplantation of a differentiated cell population to a recipient. When isolated PEDF is used, it can be mixed with a pharmaceutically acceptable carrier as necessary to formulate various preparation forms such as injection and the like, and administered to a recipient. As pharmacologically acceptable carriers, various organic or inorganic carrier substances conventionally used as preparation materials can be used, and blended as excipient, lubricant, binder, disintegrant for solid preparations; solvent, solubilizer, suspending agent, isotonizing agent, buffer, soothing agent for liquid preparations and the like. Where necessary, a preparation additive such as a preservative, an antioxidant, a colorant, a sweetener and the like can also be used.

Preferable examples of the excipient include lactose, sucrose, D-mannitol, D-sorbitol, starch, gelatinized starch, dextrin, crystalline cellulose, low-substituted hydroxypropylcellulose, sodium carboxymethylcellulose, gum arabic, pullulan, light anhydrous silicic acid, synthetic aluminum silicate, magnesium alumino metasilicate and the like.

Preferable examples of the lubricant include magnesium stearate, calcium stearate, talc, colloidal silica and the like.

Preferable examples of the binder include gelatinized starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose, polyvinylpyrrolidone and the like.

Preferable examples of the disintegrant include lactose, sucrose, starch, carboxymethylcellulose, calcium carboxymethylcellulose, croscarmellose sodium, sodium carboxymethyl starch, light anhydrous silicic acid, low-substituted hydroxypropylcellulose, and the like.

Preferable examples of the solvent include water for injection, saline, Ringer's solution, alcohol, propylene glycol, polyethylene glycol, sesame oil, corn oil, olive oil, cottonseed oil and the like.

Preferable examples of the solubilizers include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferable examples of the suspending agent include surfactant such as stearyltriethanolamine, sodium lauryl sulfate, lauryl aminopropionic acid, lecithin, benzalkonium chloride, benzethonium chloride, glycerol monostearate and the like; hydrophilic polymer such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil and the like.

Preferable examples of the isotonizing agent include sodium chloride, glycerol, D-mannitol, D-sorbitol, glucose and the like.

Preferable examples of the buffering agent include buffer such as phosphate, acetate, carbonate, citrate etc. and the like.

Preferable examples of the soothing agent include benzyl alcohol and the like.

Preferable examples of the preservative include paraoxybenzoates, chlorobutanol, benzyl alcohol, phenethyl alcohol, dehydroacetic acid, sorbic acid and the like.

Preferable examples of the antioxidant include sulfite, ascorbate and the like.

Preferable examples of the colorant include aqueous edible tar pigment (e.g., food colors such as Food Color Red Nos. 2 and 3, Food Color Yellow Nos. 4 and 5, Food Color Blue Nos. 1 and 2 etc.), water-insoluble lake dye (e.g., aluminum salt etc. of the aforementioned aqueous food tar color), natural dye (e.g., β-carotene, chlorophyll, ferric oxide red etc.) and the like.

Preferable examples of the sweetening agent include saccharin sodium, dipotassium glycyrrhizinate, aspartame, stevia and the like.

The agent for inducing apoptosis of the present invention formulated as mentioned above can be administered orally or parenterally, and preferred is parenteral administration. Specific examples thereof include injection dosage form, transnasal administration dosage form, pulmonary administration dosage form, transdermal administration dosage form and the like. As an example of the injection dosage form, the medicament can be administered systemically or locally by intravenous injection, intramuscular injection, intraperitoneal injection, subcutaneous injection and the like.

One-time dose of the agent for inducing apoptosis of the present invention can be selected from the range of, for example, 0.1-100 mg based on the amount of PEDF, which can be repetitively administered once per 1-3 days for about 1-3 months. However, the dose, administration frequency and dosing period of the agent for inducing apoptosis of the present invention are not limited thereby. The initial administration of the agent for inducing apoptosis of the present invention may be simultaneously with or before or after the cell transplantation.

On the other hand, when the agent for inducing apoptosis of the present invention is in the form of a PEDF-secreting cell, it can be formulated in the same manner as with the agent for cell transplantation therapy of the present invention. When a differentiated cell to be the cell for transplantation and a PEDF-secreting cell are of different cell types, the agent for inducing apoptosis of the present invention is desirably embedded in a biocompatible solid carrier (e.g., gel sheet), and formulated into a form which is transplanted to the affected part simultaneously with the cells for transplantation and can be removed with ease after the apoptosis induction effect of PEDF is sufficiently achieved in undifferentiated cells. Alternatively, a suicide gene such as HSV-tk gene and the like is introduced into a PEDF-secreting cell, and the cell is embedded in a solid carrier composed of a biodegradable polymer and transplanted to the affected part simultaneously with the cells for transplantation. After the apoptosis induction effect is sufficiently achieved, the PEDF-secreting cell becomes extinct by, for example, administration of gancyclovir to the recipient when HSV-tk gene is used. Therefore, removal of the cells by reoperation becomes unnecessary, and burden on the patients can be reduced.

The present invention is explained in more detail by referring to the following Examples, which are not to be construed as limitative.

EXAMPLES (Materials and Methods)

All experiments using human samples and animals were reviewed by the Institutional Review Board (IRB) of the Foundation for Biomedical Research Innovation (FBRI), RIKEN Center for Developmental Biology (RIKEN CDB), and the animal care and use committee of FBRI.

(1) Cell Culture

Human primary retina retinal pigment epithelium (RPE, Lonza) was maintained in a retinal pigment epithelial cell basal medium (Lonza Biologics, Basel, Switzerland) containing additives (L-glutamine, GA-1000 and bFGF, Lonza). Human iPS cell (iPSC) strain 253G1 (BioResource Center, RIKEN, Tsukuba) and 454E2 (see WO 2012/115244) were maintained in a human ES cell medium and 5 ng/ml bFGF (Peprotech) on feeder cell SNL (BMC Genomics (2006) 7: 248). iPSC was cultured in ReproFF2 (Reprocell) added with 5 ng/ml bFGF. iPSC-derived RPE (see WO 2012/115244) was maintained in DMEM:F12 (7:3) (Sigma-Aldrich)) added with RPE maintenance medium (B-27 additive (Invitrogen), 2 mM L-glutamine (Invitrogen), 0.5 mM SB431542 (Sigma-Aldrich) and 10 ng/ml bFGF (Wako Pure Chemical Industries).

(2) Cell Proliferation of iPSC in the Presence or Absence of Recombinant PEDF (rPEDF) or anti-PEDF Antibody 253G1 cells were seeded on 12-well transwell cell culture insert (BD) with 8 μm pore size and coated with Matrigel (BD Bioscience), and co-cultured with primary RPE or 253G1-derived RPE, seeded on the bottom of the dish, in the presence or absence of 1-50 μg/ml rPEDF (Millipore; cat # GF134 lot: DAM 1821182), 5 μg/ml anti-PEDF polyclonal antibody (BioProducts) or normal rabbit IgG (SantaCruz) in ReproFF2 medium added with bFGF. Cell proliferation of 253G1 cells in the presence or absence of 50 μg/ml rPEDF without co-culture was evaluated on days 4-6 of culture.

(3) Chip Analysis

Total RNA was isolated from 253G1 or 253G1-derived RPE by using RNAeasy Plus Mini Kit (Quiagen) according to the instructions of the manufacturer, and hybridized to Gene Chip Human Genome U133 Plus ver 2.0 (Affymetrix). The analysis data can be retrieved from GEO data set (accession Nos GSE43257).

(4) ELISA

PEDF in culture medium (conditioned medium) recovered from 24 hr culture of primary RPE or iPSC (253G1)-derived RPE was measured according to the instructions of manufacturer and using human ELISA kit (BioVendor).

Reference Example 1: Differentiation Induction from iPS Cell into RPE Cell

To establish robust differentiation protocol from pluripotent stem cell into retinal pigment epithelium (RPE), the differentiation protocol shown in FIG. 1A was used. To provide profile of reproducible iPSC-derived RPE, commercially available iPSC clone 253G1 (Nakagawa M, et al. (2008) Nat Biotechnol. 26:101-106; BioResource Center, RIKEN, Tsukuba) was used as a cell source for RPE differentiation. When cultured in a dish, RPE is a polygonal single layer cell showing sporadic pigment deposition. iPSC clone 253G1-derived RPE and primary RPE showed a similar morphology by microscopic observation (FIG. 1B). To examine whether iPSC-derived RPE shows gene expression characteristic of primary RPE, the expression of RPE65, CRALBP and bestrophin was analyzed by RT-PCR. While 253G1-derived RPE cells expressed mRNAs of RPE65, CRALBP and bestrophin, they did not express pluripotency-related genes such as Lin28, Oct3/4 and the like (FIG. 1C). ZO-1 which is a tight junction specific protein was also detected in both 253G1-derived RPE and primary RPE by immunofluorescence staining (FIG. 1D).

Figures 1, 2:
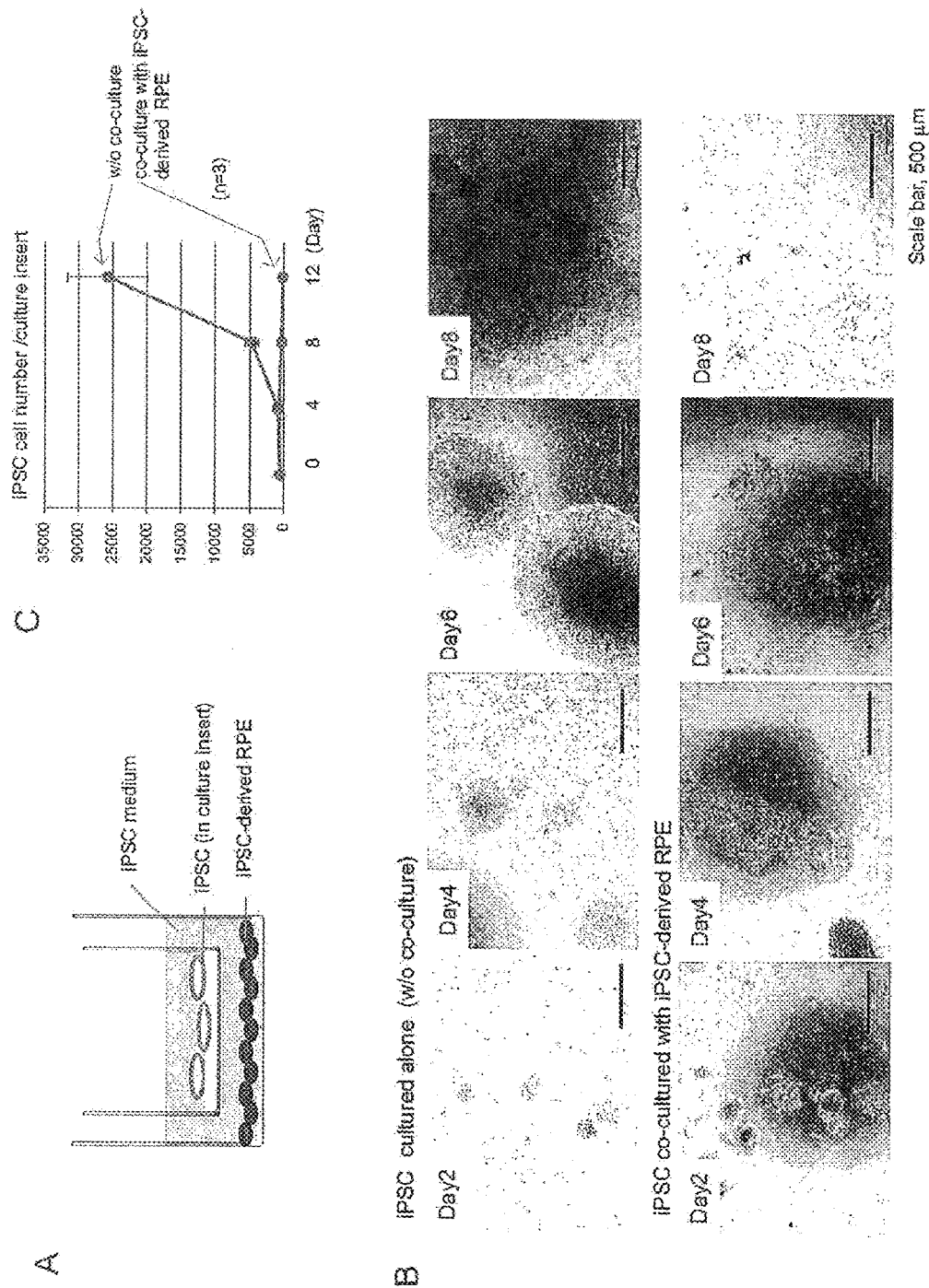
Figure 2:
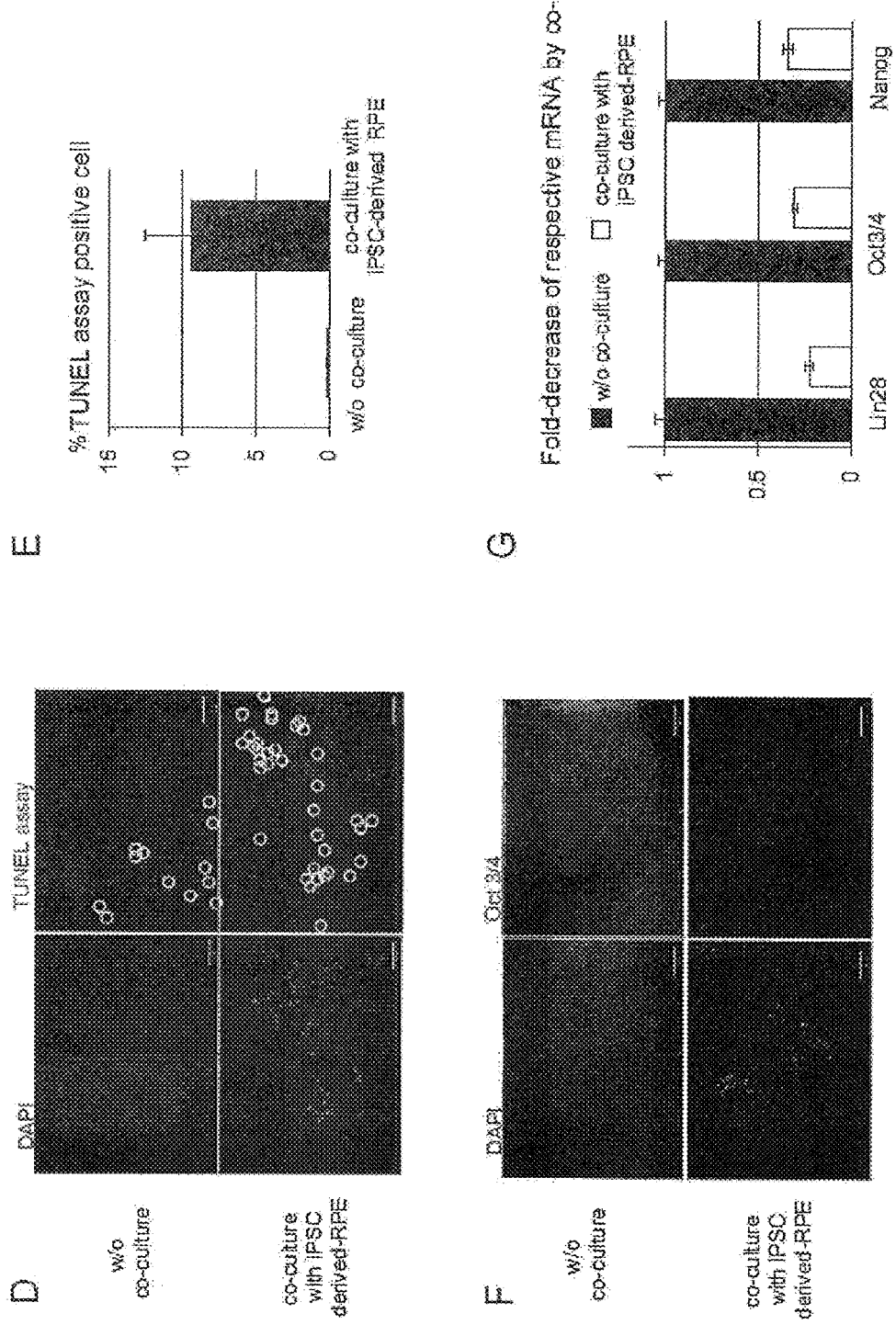
Figure 3:
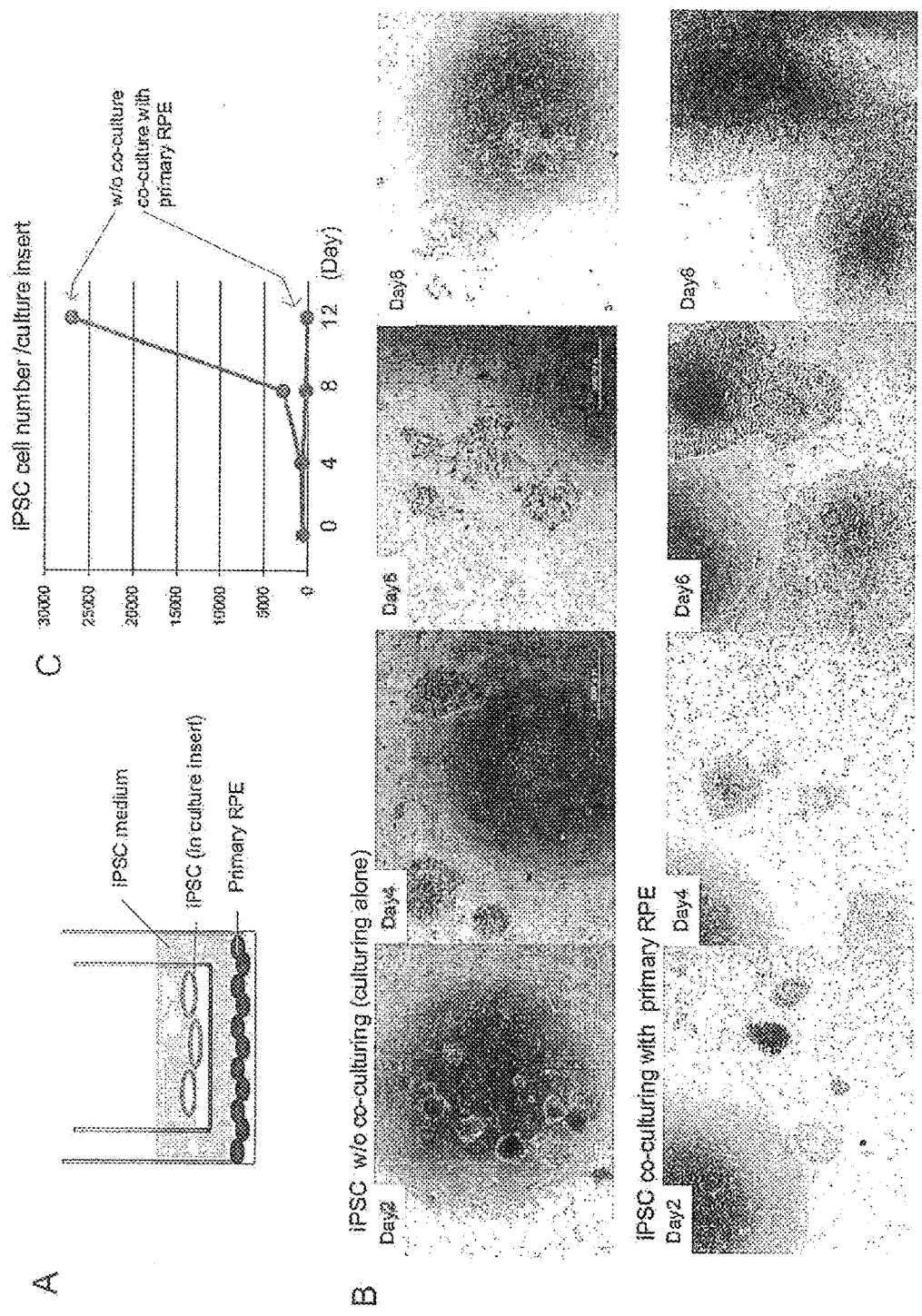
FIG. 3 shows that co-culture with primary RPE cell inhibits growth of iPS cell. (A) is a schematic showing of co-culture of iPS cell and RPE cell. (B) shows phase contrast images of iPS cell 253G1 cultured alone (upper panel) or co-cultured with primary RPE (lower panel) in 12-transwell on days 2, 4, 6 and 8 of culture. (C) shows growth curves of iPS clone 253G1 co-cultured with primary RPE cell, or cultured alone. The cell numbers of iPS clone 253G1 in 12-transwell culture on days 0, 4, 8 and 12 were counted. The mean of 3 independent experiments was plotted, and shown in a line graph with an error bar showing the standard deviation.

Example 1: Inhibition of iPS Cell Growth by Co-Culture with iPSC-Derived RPE Cell To examine an influence of a factor secreted from iPSC-derived RPE on iPS cell in vitro, the co-culture experiment shown in FIG. 2A was designed. That is, iPSC seeded on a culture insert (transwell, Corning) coated with Matrigel (BD) was co-cultured in an iPS cell medium (serum-free ReproFF added with bFGF) with iPSC-derived RPE seeded on a dish coated with CELL start (Invitrogen). iPSC in the culture insert was recovered every 4 days, and the cell number was counted. As a result, it was clarified that the growth of iPSC was markedly inhibited by co-culture with iPSC-derived RPE (FIGS. 2B, 2C). A similar trans-effect was observed even when iPSC was co-cultured with primary RPE (FIGS. 3A, B and C). The marked inhibition of the growth of iPSC co-cultured with iPSC-derived RPE was at least partially mediated by apoptotic cell death, as verified by the presence of obvious TUNEL assay positive cells (FIGS. 2D, 2E). The results of further immunostaining and quantitative RT-PCR analysis of iPSC remaining in the co-culture suggest that the expression of pluripotency-related genes such as Lin28, Oct3/4, Nanog and the like markedly decreased and iPSC-derived RPE conditioned medium promotes differentiation of iPSC (FIGS. 2F, 2g).

Based on these findings, the present inventors conducted gene chip analysis of primary RPE and 253G1-derived RPE, and parent strain iPSC clone 253G1 in an attempt to explore iPSC-derived RPE- and primary RPE-derived factor that afford a trans-effect on the growth of iPSC. The results are shown in Table 1. Some secretion factors highly expressed in both primary RPE and iPSC-derived RPE, and showing low or no expression in iPSC were extracted. They included pigment epithelium-derived factor (PEDF) reported to show an antitumor effect, vascular endothelium growth factor (VEGF) and bone morphogenic protein4 (BMP4).

TABLE 1

Key secretion factor extracted by gene chip analysis from 253G1-derived RPE or primary RPE

| | | Primary RPE | 253G1-RPE | 253G1 | hES03 |
|---|---|---|---|---|---|
| Development | | | | | |
| PEDF | pigment epithelium derived factor | 8,500 | 22,000 | 710 | 710 |
| BMP2 | bone morphogenetic protein 2 | 1,000 | 2,400 | 360 | 91 |
| VEGFB | vascular endothelial growth factor B | 300 | 500 | 190 | 98 |
| MGST2 | microsomal glutathione S-transferase 2 | 1,100 | 4,600 | 590 | 740 |
| GSTM3 | glutathione S-transferase mu 3 (brain) | 4,000 | 2,000 | 120 | 230 |
| Protease/protease inhibitor | | | | | |
| EFEMP1 | EGF-containing fibulin-like extracellular matrix protein 1 | 4,200 | 2,100 | 0.70 | 240 |
| PLOD2 | procollagen-lysine, 2-oxoglutarate 5-dioxygenase 2 | 6,300 | 2,900 | 700 | 840 |
| MMP14 | matrix metallopeptidase 14 (membrane-inserted) | 1,900 | 1,000 | 160 | 150 |
| CPA4 | Carboxypentidase A4 | 1,100 | 1,900 | 17 | 74 |
| Cell adhesion/connective tissue protein | | | | | |
| COL3A1 | collagen, type III, alpha 1 | 5,100 | 3,900 | 35 | 950 |
| SEMA3C | sema domain, immunoglobulin domain (Ig), short basic domaine, secreted, (semaphorin) 3C | 7,400 | 4,900 | 31 | 79 |

TABLE 1-continued

Key secretion factor extracted by gene chip analysis from 253G1-derived RPE or primary RPE

| | | Primary RPE | 253G1-RPE | 253G1 | hES03 |
|---|---|---|---|---|---|
| Complement regulator/immune response | | | | | |
| CFI | complement factor I | 2,600 | 5,100 | 0.40 | 46 |
| APPBP2 | amyloid beta precursor protein (cytoplasmic tail) binding protein 2 | 2,100 | 2,200 | 300 | 500 |

Example 2: Induction of Apoptotic Cell Death of iPS Cell by PEDF

Figures 1, 4:
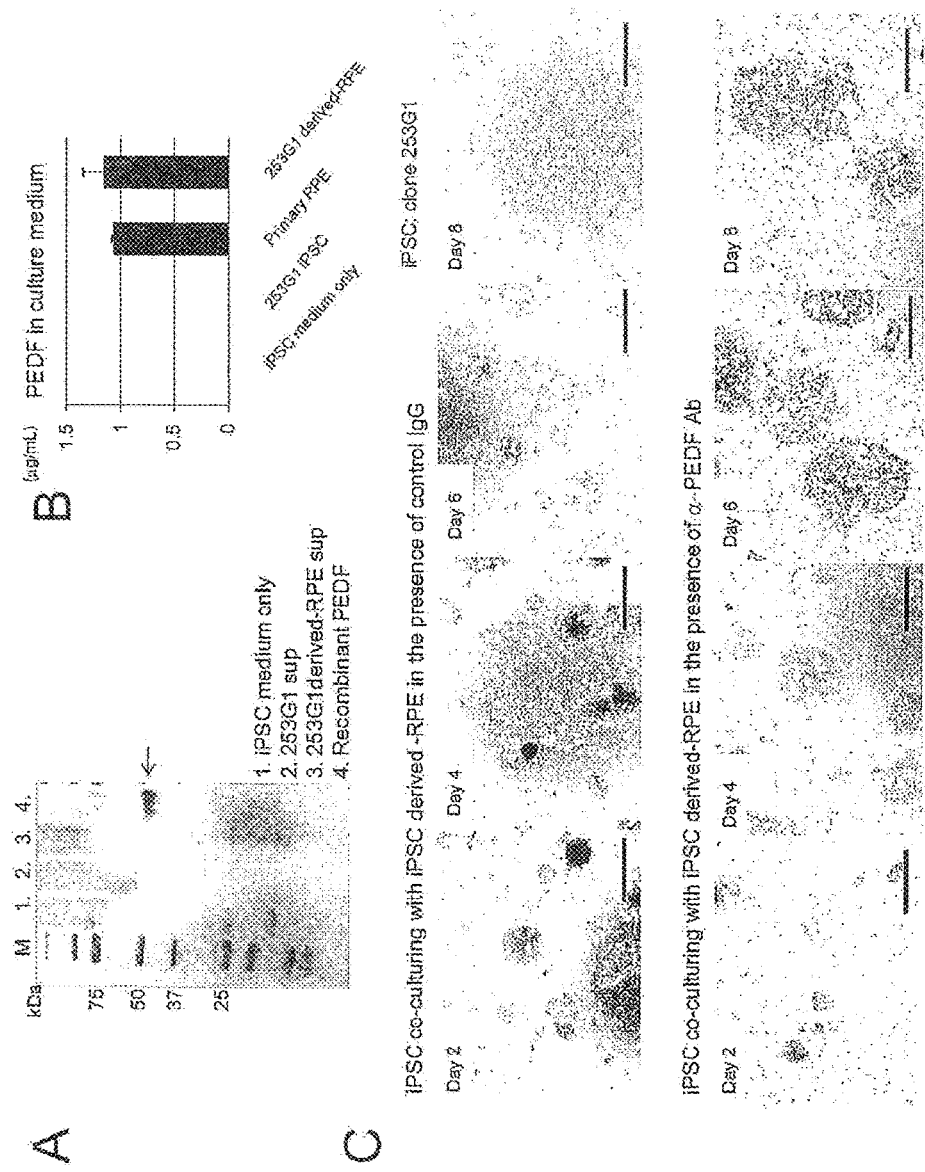
Figures 2, 4:
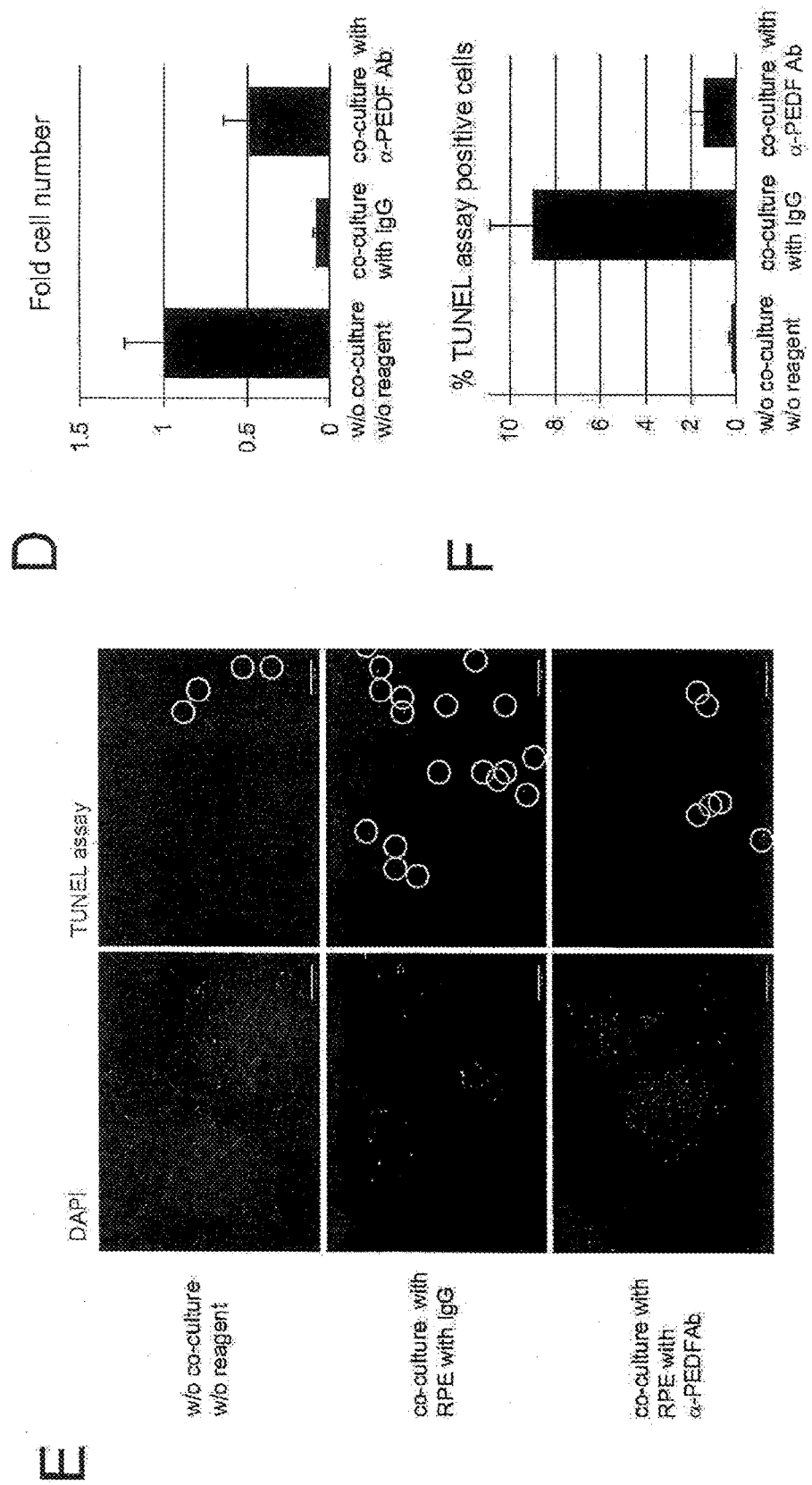
Figure 4:
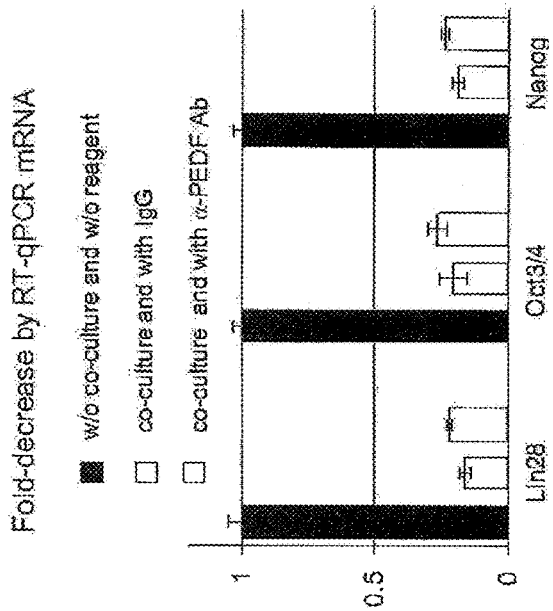
Figure 3:
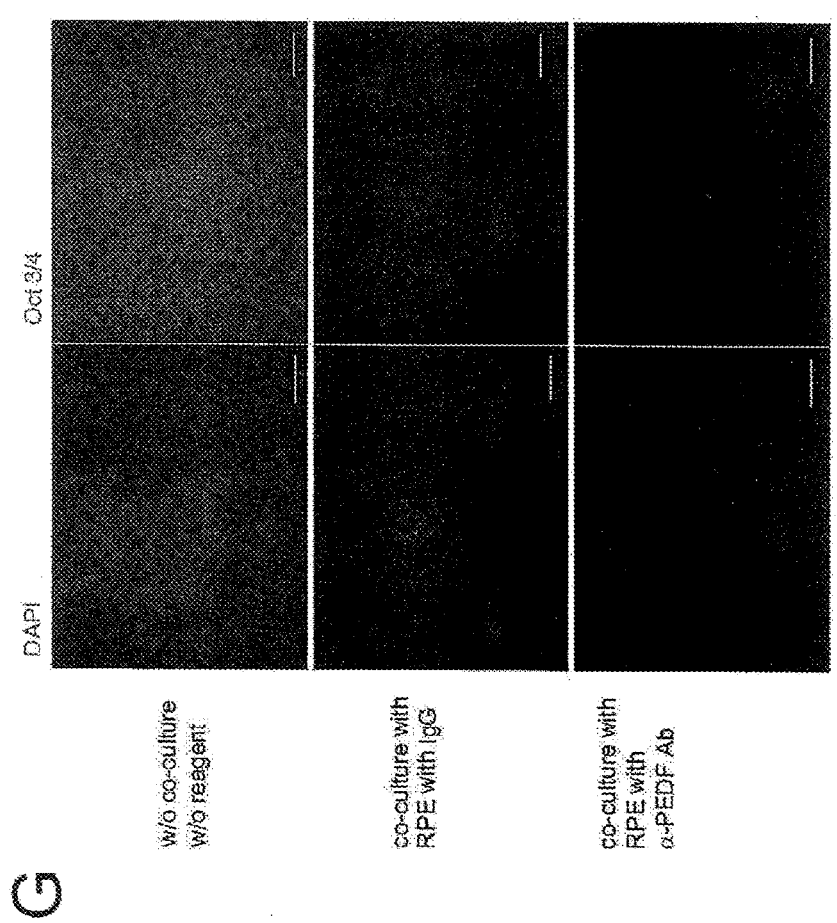

PEDF protein in an iPSC-derived RPE conditioned medium was detected by Western blotting using an anti-PEDF antibody (BioProducts, MD) (FIG. 4A). A fresh iPS cell medium free of co-culture was used as a control sample. The PEDF level in 24 hr of cell culture (24 hr after exchange with fresh medium) was measured by ELISA. Both the primary RPE conditioned medium and iPSC-derived conditioned medium contained a considerable amount of PEDF (exceeding 1 μg/ml) (FIG. 4B).

Therefore, an influence of PEDF on the growth of iPSC was tested. An anti-PEDF neutralizing antibody (BioProducts, MD) was added to the co-culture system, and the growth of iPSC in the culture insert was examined. The growth of 253G1 co-cultured with 253G1-derived RPE was markedly inhibited in the presence of control IgG, but such inhibition of cell proliferation was considerably blocked in the presence of an anti-PEDF antibody (FIG. 4C). Although the dose and species of the anti-PEDF neutralizing antibody were not optimized, almost half the number of iPSC was rescued by the addition of the anti-PEDF antibody (FIG. 4D). The results suggest that apoptotic cell death of iPSC is blocked by an anti-PEDF neutralizing antibody (FIGS. 4E, 4F). However, the expression of pluripotency-related protein Oct3/4 decreased even in the presence of an anti-PEDF antibody (FIG. 4g), and the mRNA expression of Lin28, Oct3/4 and Nanog also decreased (FIG. 4H). It is interesting that the differentiation of 253G1 cell was not inhibited by the addition of an anti-PEDF antibody during co-culture with 253G1-derived RPE. These results suggest a possibility that a secretion factor from RPE other than PEDF may promote differentiation of surviving iPSC.

Figures 1, 5:
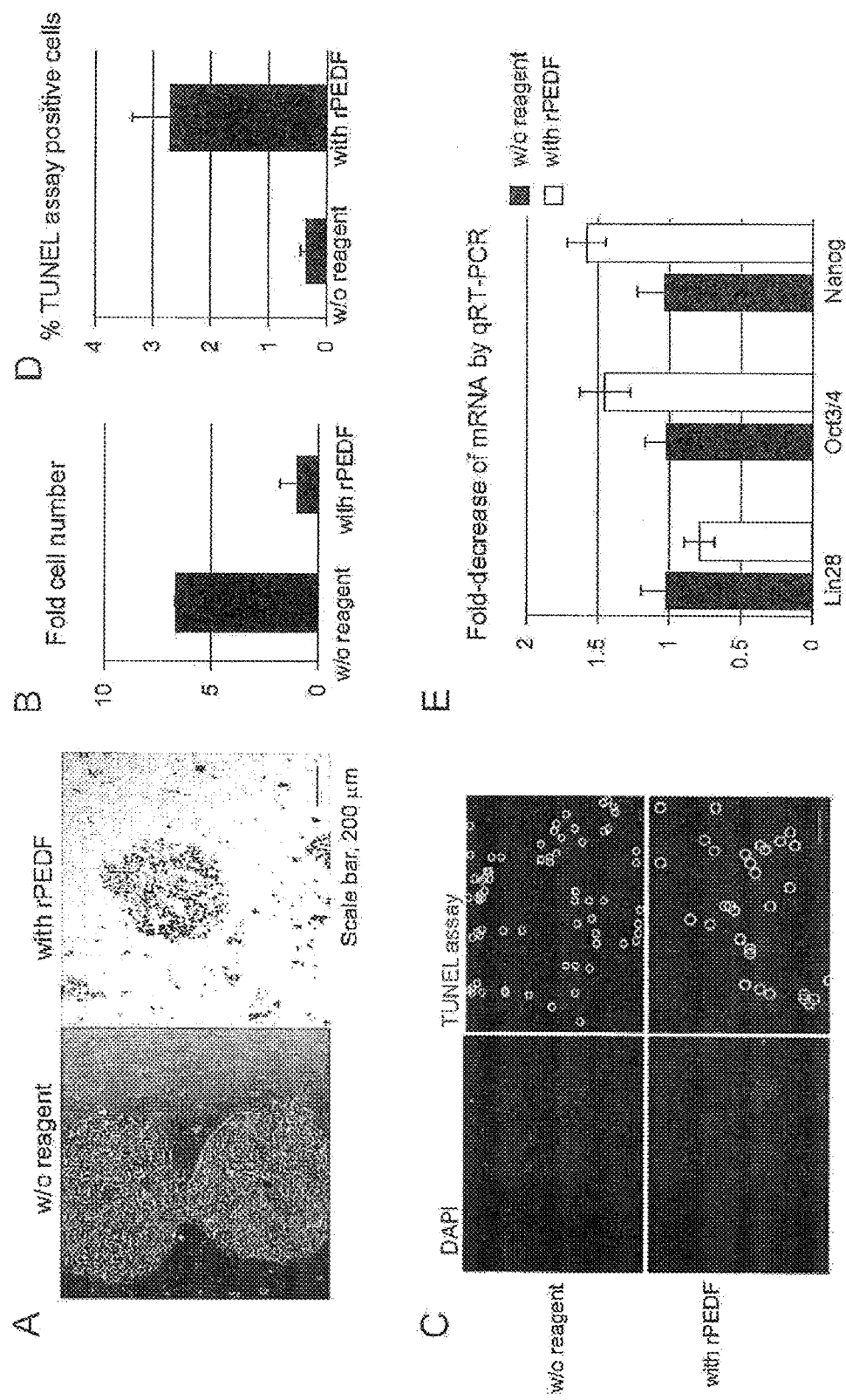
Figures 2, 5:

To examine an influence of PEDF on the growth of iPSC, recombinant PEDF protein (rPEDF) was used. 50 μg/ml of rPEDF inhibited the growth of iPSC (FIGS. 5A, 5B), and induced the apoptotic cell death as demonstrated by TUNEL assay (FIGS. 5C, 5D). 50 μg/ml of rPEDF also induced apoptotic cell death of human ES cell (KhES-1) (FIG. 6). The morphology of iPSC remaining after the addition of rPEDF was the same as that of untreated iPSC (FIG. 5A). Furthermore, a decrease in the mRNA expression of pluripotency-related genes Lin28, Oct3/4 and Nanog was not observed in the remaining cells (FIG. 5E). The cell numbers after the rPEDF treatment, which were obtained by counting DAPI positive cells, was not constant. This may explain upregulation of the pluripotency-related gene mRNA after the rPEDF addition. Then, a signal transduction pathway that causes apoptosis of iPSC via PEDF was examined. As a result of Western blotting, phosphorylation of p38 MAP kinase and cleaved caspase-3 molecules were detected after rPEDF stimulation of iPSC, which is consistent with the previous report (Gonzaleza R, et al (2010) Proc. Natl. Acad. Sci. USA. 107 3552-3557) (FIGS. 5F, 5g).

When these results are taken together, PEDF is considered to induce apoptotic cell death of iPSC, but not induce differentiation of iPSC.

Figure 7:
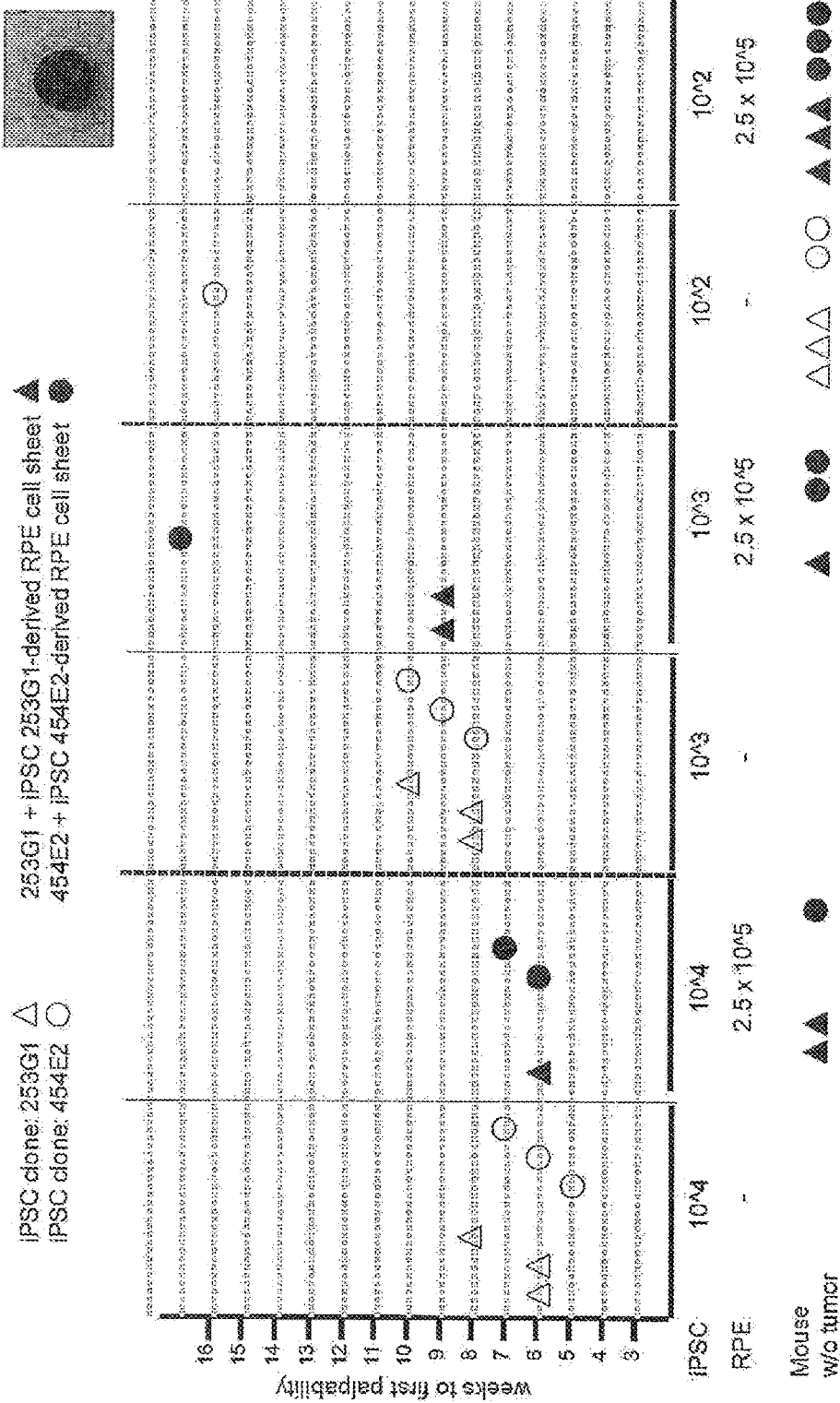
FIG. 7 shows a tumor formation suppressive effect of PEDF in vivo. $10^2$, $10^3$ and $10^4$ cells of iPSC clones 253G1 and 454E2 were subcutaneously transplanted simultaneously to NOG mice (each group 3 mice) together with 253G1 and 454E2-derived RPE cell sheets (containing about $2.5 \times 10^5$ RPE cells), respectively. The vertical axis shows the week when tumor was first detected in each case. The horizontal axis shows the numbers of iPSC and iPSC-derived RPE cells. The number of mice that did not form tumor is shown with respective symbols below the horizontal axis. The photograph on the upper right shows RPE cell sheet in 24-well plate. The number of iPSC cells necessary for 50% tumor growth ($TPD_{50}$ $\log_{10}$) with or without RPE is shown below each graph. P value between with RPE cell and without RPE cell was less than 0.001. P<0.05 was regarded significant. Supposing mouse without tumor on week 30 formed tumor on week 31, the statistics was taken by SigmaPlot Ver. 11.0 (manufactured by Systat Software Inc.).

Example 3: Suppression of Tumor Formation from iPSC by Simultaneous Transplantation of RPE Cell Sheet In clinical situations, one or two RPE cell sheets (1.3 mm×3 mm in size) containing about 2-5×$10^4$ RPE cells are transplanted to the retina of age-related macular degeneration patients. It is an important problem after transplantation to eliminate the possibility of tumor formation from undifferentiated iPSC or insufficiently differentiated cells remaining in an iPSC-derived cell product. Therefore, to evaluate the trans-effect of RPE on iPSC remaining in retina after transplantation, the present inventors performed an iPSC spike test in the presence of RPE sheet using an immunodeficient animal model and examined the tumor formation capacity of iPSC. RPE sheet was prepared on a collagen gel according to the method described in WO 2012/115244. As a preliminary experiment, some doses of iPSC were subcutaneously or intraretinally injected to various immunodeficient animal models including nude rat (F344/NJc1-rnu/rnu) and nude mouse (BALB/cA, JC1-nu/nu, SCID: C.B-17/Icr-scid/scid, Jc1, NOD-SCID: NOD/ShiJic-scid, Jc1, NOG: NOD/ShiJic-scid, IL-2Rg KO Jic). As a result, NOG mouse showed the highest sensitivity for tumor formation from iPSC and HeLa cell when subcutaneously injected together with Matrigel (BD), which was consistent with a previous report (J Biol Chem 277(11): 9492-7, 2002). Thus, $10^2$, $10^3$ or $10^4$ iPSC (clone 253G1 or 454E2) were subcutaneously transplanted together with 253G1- or 454E2-derived RPE cell sheet (containing about 2×$10^5$ RPE cells) to NOG mouse, and tumor formation was examined. As a result, when $10^3$ or $10^4$ iPSC were transplanted, the mouse simultaneously transplanted with RPE showed markedly decreased tumor formation frequency as compared to the mouse free of transplantation of RPE (FIG. 7). Detection of a significant difference between the RPE transplantation group and the RPE non-transplantation group was performed by ANOVA. As a result, a significant difference was found between the two groups when $10^3$ or $10^4$ iPSC were transplanted (P<0.01).

Example 4: Study of PEDF Sensitivity of Various Differentiated Cells

As various cultured cells (differentiated cells), P1-P3 of the following cells (human cardiac muscle cell (Human Cardiac Myocytes, Cat. 6200, ScienCell), human chondrocyte (NB6) and human hepatocyte (Human Hepatocytes, Cat. 5200, ScienCell)) were used. In a medium for each cell (Cardiac Myocytes Medium, Cat. 6201, DMEM/F12 containing Gluta Max, 2013-06, Gibco and Hepatocyte Medium, Cat. 5201), mature iPSC-derived RPE cells were cultured for 48 hr to give each conditioned medium. In parallel, the above-mentioned each differentiated cells were seeded on 8-well chamber slide at 20,000 cells/chamber, and cultured overnight in a medium for each cell. Then, the medium was exchanged with the above-mentioned each conditioned medium, or a medium for each cell added with recombinant PEDF at a concentration of 50 µg/ml. Each medium was exchanged every 48 hr.

Figure 8:
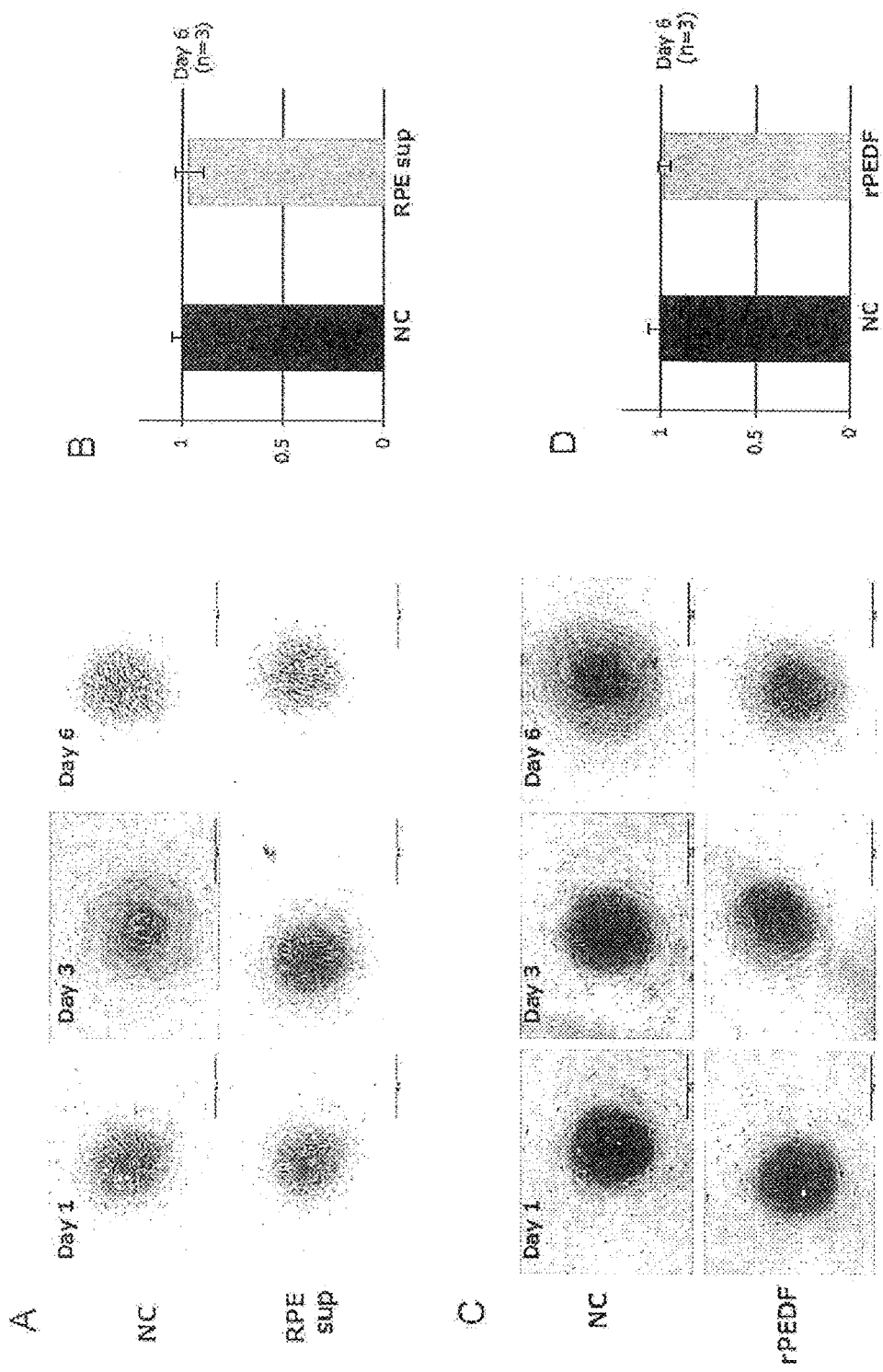
FIG. 8 shows an influence of PEDF on the growth of human cardiac muscle cell. (A) shows phase contrast images of human cardiac muscle cell cultured in a general cardiac muscle cell medium (NC; upper panel) or an iPSC-derived RPE cell conditioned medium (RPE sup; lower panel) on days 1, 3 and 6 of culture. (B) The cell number of human cardiac muscle cells cultured in an iPSC-derived RPE cell conditioned medium or a general cardiac muscle cell medium was counted on day 6 of culture. The mean of 3 independent experiments is shown in a bar graph as relative value to the number of cells cultured alone as 1. The error bar shows standard deviation. (C) shows phase contrast images of human cardiac muscle cell cultured in the presence of rPEDF (50 µg/ml) (ePEDF; lower panel) or absence thereof (NC; upper panel) on days 1, 3 and 6 of culture. (D) The cell number of human cardiac muscle cells cultured in the presence or absence of rPEDF (50 µg/ml) was counted on day 6 of culture. The mean of 3 independent experiments is shown in a bar graph as relative value to the number of cells cultured alone as 1. The error bar shows standard deviation.
Figure 9:
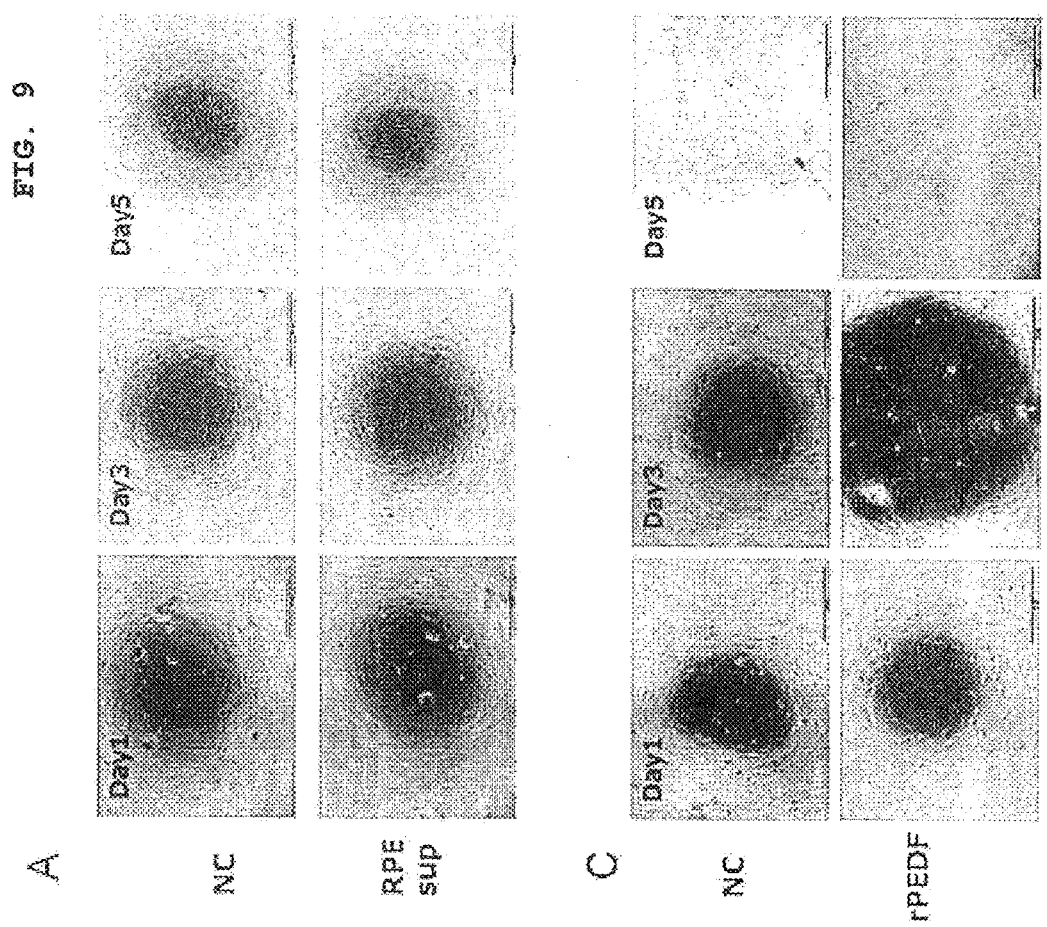
FIG. 9 shows an influence of PEDF on the growth of human chondrocyte. (A) shows phase contrast images of human chondrocyte cultured in a general chondrocyte medium (NC; upper panel) or an iPSC-derived RPE cell conditioned medium (RPE sup; lower panel) on days 1, 3 and 5 of culture. (B) The cell number of human chondrocytes cultured in an iPSC-derived RPE cell conditioned medium or a general chondrocyte medium was counted on day 5 of culture. The mean of 3 independent experiments is shown in a bar graph as relative value to the number of cells cultured alone as 1. The error bar shows standard deviation. (C) shows phase contrast images of human chondrocyte cultured in the presence of rPEDF (50 µg/ml) (ePEDF; lower panel) or absence thereof (NC; upper panel) on days 1, 3 and 5 of culture. (D) The cell number of human chondrocytes cultured in the presence or absence of rPEDF (50 µg/ml) was counted on day 5 of culture. The mean of 3 independent experiments is shown in a bar graph as relative value to the number of cells cultured alone as 1. The error bar shows standard deviation.
Figure 10:
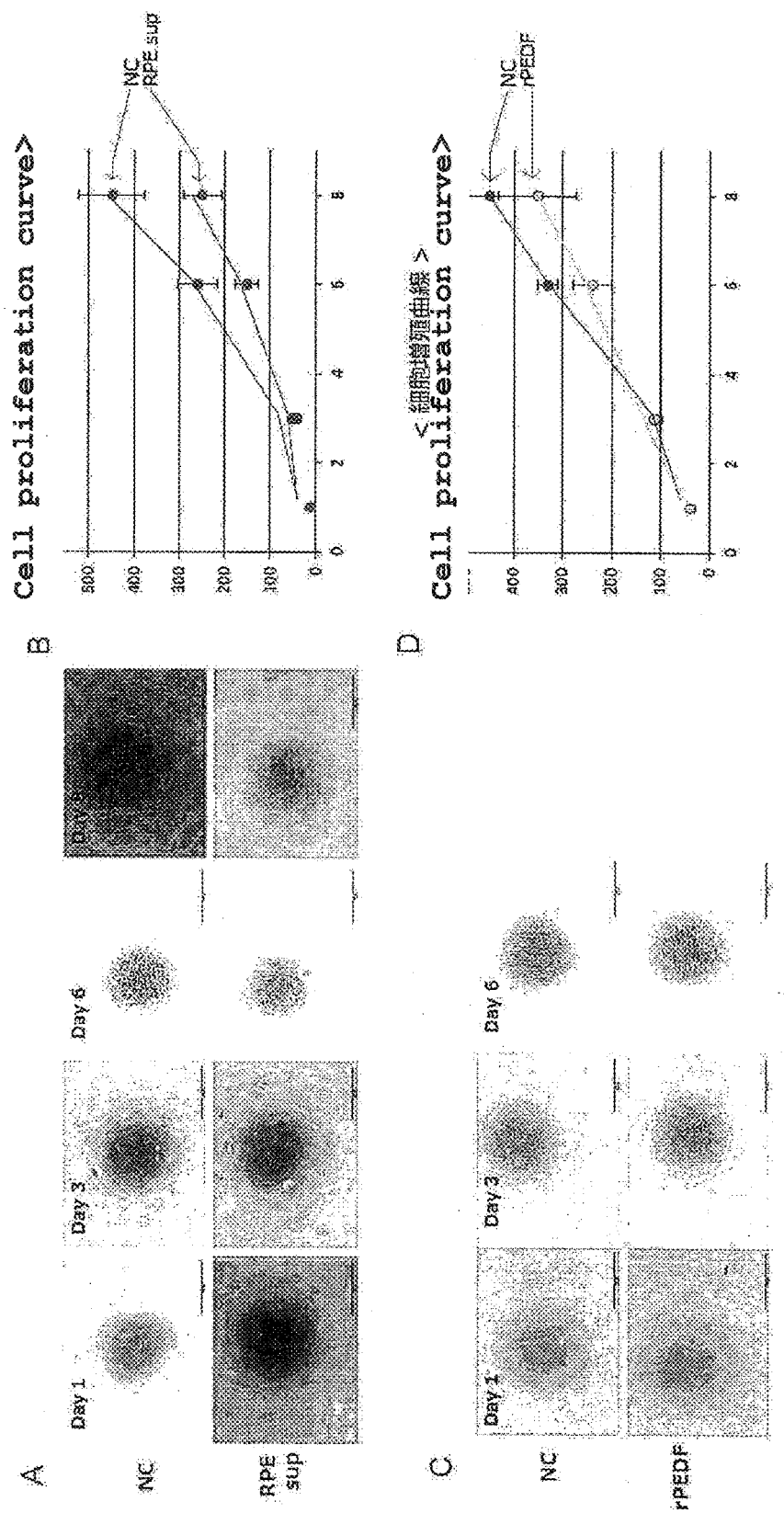
FIG. 10 shows an influence of PEDF on the growth of human hepatocytes. (A) shows phase contrast images of human hepatocyte cultured in a general hepatocyte medium (NC; upper panel) or an iPSC-derived RPE cell conditioned medium (RPE sup; lower panel) on days 1, 3, 6 and 8 of culture. (B) shows growth curves of human hepatocytes cultured in an iPSC-derived RPE cell conditioned medium or a general hepatocyte medium. The cell number of human hepatocytes was counted on days 1, 3, 6 and 8 of culture. The mean of 3 independent experiments was plotted, and shown in a line graph with an error bar showing the standard deviation. (C) shows phase contrast images of human hepatocyte cultured in the presence of rPEDF (50 µg/ml) (ePEDF; lower panel) or absence thereof (NC; upper panel) on days 1, 3, 6 and 8 of culture. (D) shows growth curves of human hepatocytes cultured in the presence or absence of rPEDF (50 µg/ml). The cell number of human hepatocytes was counted on days 1, 3, 6 and 8 of culture. The mean of 3 independent experiments was plotted, and shown in a line graph with an error bar showing the standard deviation.

Cardiac muscle cells were recovered on days 1, 3 and 6 of culture, chondrocytes were recovered on days 1, 3 and 5 of culture, and hepatocytes were recovered on days 1, 3, 6 and 8 of culture, and the cell number was counted. The results are shown in FIGS. 8-10. Cardiac muscle cells and chondrocytes did not show an influence on cell proliferation in both the iPSC-derived RPE cell conditioned medium and the recombinant PEDF addition medium (FIGS. 8 and 9). On the other hand, hepatocytes showed a decrease in the cell proliferation rate in both the iPSC-derived RPE cell conditioned medium and the recombinant PEDF addition medium, but did not show remarkable apoptosis (FIG. 10).

The above shows that the cell sorting method using PEDF in the present invention is applicable to the selective removal of not only RPE but also undifferentiated cells contaminating various differentiated cell populations.

INDUSTRIAL APPLICABILITY

According to the sorting method of the present invention, since PEDF induces apoptosis of undifferentiated cells, a treatment with PEDF after induction of undifferentiated cells into differentiated cells of interest removes undifferentiated cells, and increases the purity of the obtained differentiated cells to enable safe administration to the administration subject. Particularly, since administration of undifferentiated cell may result in canceration, the present invention is extremely important for reducing the risk of canceration in regenerative medicine.

This application is based on a patent application No. 2013-062765 filed in Japan (filing date: Mar. 25, 2013), the contents of which are hereby incorporated by reference in full herein.

The invention claimed is:

1. A method of removing or reducing undifferentiated cells from a differentiated cell population that is contaminated or has a risk of contamination with undifferentiated cells, comprising contacting a recombinant pigment epithelium-derived factor (PEDF) with the differentiated cell population in a culture medium, and verifying that the resulting cell population is substantially free of the undifferentiated cell,
wherein the undifferentiated cell is an induced pluripotent stem (iPS) cell or an embryonic stem (ES) cell,
wherein the differentiated cell is other than a vascular endothelial cell and a corneal epithelial cell, and
wherein the method induces apoptosis of the undifferentiated cell.

2. The method according to claim 1, wherein the undifferentiated cell is a pluripotent stem cell having differentiation potency into three germ layer lineages.

3. The method according to claim 2, wherein the undifferentiated cell further expresses one or more undifferentiated markers selected from the group consisting of Lin28, Oct3/4 and Nanog.

4. The method according to claim 1, wherein the differentiated cell is a cell selected from the group consisting of skin cell, eye cell, brain cell, hair cell, mouth cavity mucous membrane, lung cell, hepatocyte, stomach mucosal cell, gut cell, splenocyte, pancreatic cell, kidney cell, blood cell, peripheral blood mononuclear cell, peripheral blood lymphocyte, cord blood cell, retinal pigment epithelium, myocyte, cardiac muscle cell, chondrocyte, fibroblast, neural stem cell, hematopoietic stem cell, mesenchymal stem cell, spermatogonial stem cell, and muscle stem cell.

5. The method according to claim 1, wherein the differentiated cell is a cell selected from the group consisting of retinal pigment epithelium, cardiac muscle cell, chondrocyte, and hepatocyte.

6. The method according to claim 1, which does not induce apoptosis of the differentiated cell.

7. The method according to claim 1, wherein the differentiated cell population is obtained by differentiation induction of undifferentiated cells.

8. The method according to claim 1, wherein the verification comprises culturing the differentiated cell population under undifferentiating conditions and detecting development of an undifferentiated cell by utilizing properties specific to the undifferentiated cell.

9. The method according to claim 1, wherein the verification comprises detecting expression of an undifferentiation specific antigen or gene.

10. A method of removing or reducing undifferentiated cells from a differentiated cell population that is contaminated or has a risk of contamination with undifferentiated cells, comprising contacting a separated conditioned medium comprising a pigment epithelium-derived factor (PEDF) with the differentiated cell population, and verifying that the resulting cell population is substantially free of the undifferentiated cell,
wherein the undifferentiated cell is an induced pluripotent stem (iPS) cell or an embryonic stem (ES) cell,
wherein the differentiated cell is other than a vascular endothelial cell and a corneal epithelial cell,
and
wherein the method induces apoptosis of the undifferentiated cell.

11. The method according to claim 10, wherein the undifferentiated cell is a pluripotent stem cell having differentiation potency into three germ layer lineages.

12. The method according to claim 11, wherein the undifferentiated cell further expresses one or more undifferentiated markers selected from the group consisting of Lin28, Oct3/4 and Nanog.

13. The method according to claim 10, wherein the differentiated cell is a cell selected from the group consisting of skin cell, eye cell, brain cell, hair cell, mouth cavity mucous membrane, lung cell, hepatocyte, stomach mucosal cell, gut cell, splenocyte, pancreatic cell, kidney cell, blood cell, peripheral blood mononuclear cell, peripheral blood lymphocyte, cord blood cell, retinal pigment epithelium, myocyte, cardiac muscle cell, chondrocyte, fibroblast, neural stem cell, hematopoietic stem cell, mesenchymal stem cell, spermatogonial stem cell, and muscle stem cell.

14. The method according to claim 10, wherein the differentiated cell is a cell selected from the group consisting of retinal pigment epithelium, cardiac muscle cell, chondrocyte, and hepatocyte.

15. The method according to claim 10, which does not induce apoptosis of the differentiated cell.

16. The method according to claim 10, wherein the differentiated cell population is obtained by differentiation induction of undifferentiated cells.

17. The method according to claim 10, wherein the verification comprises culturing the differentiated cell population under undifferentiating conditions and detecting development of an undifferentiated cell by utilizing properties specific to the undifferentiated cell.

18. The method according to claim 10, wherein the verification comprises detecting expression of an undifferentiation specific antigen or gene.

* * * * *

UNITED STATES PATENT AND TRADEMARK OFFICE
CERTIFICATE OF CORRECTION

PATENT NO. : 10,072,242 B2
APPLICATION NO. : 14/780324
DATED : September 11, 2018
INVENTOR(S) : Kanemura et al.

It is certified that error appears in the above-identified patent and that said Letters Patent is hereby corrected as shown below:

In the Drawings

Sheet 14, Fig. 10, view C, delete the character ">" after the word "curve"

Sheet 14, Fig. 10, view D, delete "< ▒▒▒▒▒▒ >" immediately above the text "Cell proliferation curve>", and delete the character ">" after the word "curve"

In the Specification

In the description

Column 7, Line 45, "Sa114" should read "Sall4"

Column 8, Line 8, delete "to"

Column 8, Line 13, delete "is"

Column 9, Line 30, "Tc11" should read "Tcl1"

Column 9, Line 31, "Sa111" should read "Sall1"

Column 9, Line 31, "Sa114" should read "Sall4"

Column 10, Line 9, "SctDB1" should read "Suv39h2,"

Column 13, Line 18, delete "(D) Induced Pluripotent Stem Cell"

Column 15, Line 22, "aMEM" should read "αMEM"

Signed and Sealed this
Nineteenth Day of February, 2019

Andrei Iancu
*Director of the United States Patent and Trademark Office*

CERTIFICATE OF CORRECTION (continued)
U.S. Pat. No. 10,072,242 B2

Column 16, Line 4, delete the word "to"

Column 16, Line 8, delete the word "is"

Column 22, Table 1, last line, "domaine" should read "domain"

Column 24, Line 36, "(F344/NJc1-rnu/rnu)" should read "(F344/NJcl-rnu/rnu)"

Column 24, Line 38, "Jc1" should read "Jcl"

SEQUENCE LISTING

```
<160> NUMBER OF SEQ ID NOS: 2

<210> SEQ ID NO 1
<211> LENGTH: 1257
<212> TYPE: DNA
<213> ORGANISM: Homo sapiens
<220> FEATURE:
<221> NAME/KEY: CDS
<222> LOCATION: (1)..(1254)
<220> FEATURE:
<221> NAME/KEY: sig_peptide
<222> LOCATION: (1)..(57)
<220> FEATURE:
<221> NAME/KEY: mat_peptide
<222> LOCATION: (58)..(1254)

<400> SEQUENCE: 1 atg cag gcc ctg gtg cta ctc ctc tgc att gga gcc ctc ctc ggg cac        48
Met Gln Ala Leu Val Leu Leu Leu Cys Ile Gly Ala Leu Leu Gly His
            -15                 -10                  -5 agc agc tgc cag aac cct gcc agc ccc ccg gag gag ggc tcc cca gac        96
Ser Ser Cys Gln Asn Pro Ala Ser Pro Pro Glu Glu Gly Ser Pro Asp
     -1   1               5                  10 ccc gac agc aca ggg gcg ctg gtg gag gag gag gat cct ttc ttc aaa       144
Pro Asp Ser Thr Gly Ala Leu Val Glu Glu Glu Asp Pro Phe Phe Lys
         15                  20                  25 gtc ccc gtg aac aag ctg gca gcg gct gtc tcc aac ttc ggc tat gac       192
Val Pro Val Asn Lys Leu Ala Ala Ala Val Ser Asn Phe Gly Tyr Asp
 30                  35                  40                  45 ctg tac cgg gtg cga tcc agc acg agc ccc acg acc aac gtg ctc ctg       240
Leu Tyr Arg Val Arg Ser Ser Thr Ser Pro Thr Thr Asn Val Leu Leu
                 50                  55                  60 tct cct ctc agt gtg gcc acg gcc ctc tcg gcc ctc tcg ctg gga gcg       288
Ser Pro Leu Ser Val Ala Thr Ala Leu Ser Ala Leu Ser Leu Gly Ala
             65                  70                  75 gag cag cga aca gaa tcc atc att cac cgg gct ctc tac tat gac ttg       336
Glu Gln Arg Thr Glu Ser Ile Ile His Arg Ala Leu Tyr Tyr Asp Leu
         80                  85                  90 atc agc agc cca gac atc cat ggt acc tat aag gag ctc ctt gac acg       384
Ile Ser Ser Pro Asp Ile His Gly Thr Tyr Lys Glu Leu Leu Asp Thr
     95                 100                 105 gtc act gcc ccc cag aag aac ctc aag agt gcc tcc cgg atc gtc ttt       432
```

-continued

| | | | | | | | | | | | | | | | |
|---|---|---|---|---|---|---|---|---|---|---|---|---|---|---|---|
| | Val | Thr | Ala | Pro | Gln | Lys | Asn | Leu | Lys | Ser | Ala | Ser | Arg | Ile | Val | Phe |
| | 110 | | | | 115 | | | | | 120 | | | | | 125 |

```
gag aag aag ctg cgc ata aaa tcc agc ttt gtg gca cct ctg gaa aag      480
Glu Lys Lys Leu Arg Ile Lys Ser Ser Phe Val Ala Pro Leu Glu Lys
                130                 135                 140 tca tat ggg acc agg ccc aga gtc ctg acg ggc aac cct cgc ttg gac      528
Ser Tyr Gly Thr Arg Pro Arg Val Leu Thr Gly Asn Pro Arg Leu Asp
            145                 150                 155 ctg caa gag atc aac aac tgg gtg cag gcg cag atg aaa ggg aag ctc      576
Leu Gln Glu Ile Asn Asn Trp Val Gln Ala Gln Met Lys Gly Lys Leu
        160                 165                 170 gcc agg tcc aca aag gaa att ccc gat gag atc agc att ctc ctt ctc      624
Ala Arg Ser Thr Lys Glu Ile Pro Asp Glu Ile Ser Ile Leu Leu Leu
    175                 180                 185 ggt gtg gcg cac ttc aag ggg cag tgg gta aca aag ttt gac tcc aga      672
Gly Val Ala His Phe Lys Gly Gln Trp Val Thr Lys Phe Asp Ser Arg
190                 195                 200                 205 aag act tcc ctc gag gat ttc tac ttg gat gaa gag agg acc gtg agg      720
Lys Thr Ser Leu Glu Asp Phe Tyr Leu Asp Glu Glu Arg Thr Val Arg
                210                 215                 220 gtc ccc atg atg tcg gac cct aag gct gtt tta cgc tat ggc ttg gat      768
Val Pro Met Met Ser Asp Pro Lys Ala Val Leu Arg Tyr Gly Leu Asp
            225                 230                 235 tca gat ctc agc tgc aag att gcc cag ctg ccc ttg acc gga agc atg      816
Ser Asp Leu Ser Cys Lys Ile Ala Gln Leu Pro Leu Thr Gly Ser Met
        240                 245                 250 agt atc atc ttc ttc ctg ccc ctg aaa gtg acc cag aat ttg acc ttg      864
Ser Ile Ile Phe Phe Leu Pro Leu Lys Val Thr Gln Asn Leu Thr Leu
    255                 260                 265 ata gag gag agc ctc acc tcc gag ttc att cat gac ata gac cga gaa      912
Ile Glu Glu Ser Leu Thr Ser Glu Phe Ile His Asp Ile Asp Arg Glu
270                 275                 280                 285 ctg aag acc gtg cag gcg gtc ctc act gtc ccc aag ctg aag ctg agt      960
Leu Lys Thr Val Gln Ala Val Leu Thr Val Pro Lys Leu Lys Leu Ser
                290                 295                 300 tat gaa ggc gaa gtc acc aag tcc ctg cag gag atg aag ctg caa tcc     1008
Tyr Glu Gly Glu Val Thr Lys Ser Leu Gln Glu Met Lys Leu Gln Ser
            305                 310                 315 ttg ttt gat tca cca gac ttt agc aag atc aca ggc aaa ccc atc aag     1056
Leu Phe Asp Ser Pro Asp Phe Ser Lys Ile Thr Gly Lys Pro Ile Lys
        320                 325                 330 ctg act cag gtg gaa cac cgg gct ggc ttt gag tgg aac gag gat ggg     1104
Leu Thr Gln Val Glu His Arg Ala Gly Phe Glu Trp Asn Glu Asp Gly
    335                 340                 345 gcg gga acc acc ccc agc cca ggg ctg cag cct gca cac ctc acc ttc     1152
Ala Gly Thr Thr Pro Ser Pro Gly Leu Gln Pro Ala His Leu Thr Phe
350                 355                 360                 365 ccg ctg gac tat cac ctt aac cag cct ttc atc ttc gta ctg agg gac     1200
Pro Leu Asp Tyr His Leu Asn Gln Pro Phe Ile Phe Val Leu Arg Asp
                370                 375                 380 aca gac aca ggg gcc ctt ctc ttc att ggc aag att ctg gac ccc agg     1248
Thr Asp Thr Gly Ala Leu Leu Phe Ile Gly Lys Ile Leu Asp Pro Arg
            385                 390                 395 ggc ccc taa                                                          1257
Gly Pro
```

<210> SEQ ID NO 2
<211> LENGTH: 418
<212> TYPE: PRT
<213> ORGANISM: Homo sapiens

<400> SEQUENCE: 2

Met Gln Ala Leu Val Leu Leu Leu Cys Ile Gly Ala Leu Leu Gly His
                -15                 -10                  -5

Ser Ser Cys Gln Asn Pro Ala Ser Pro Pro Glu Glu Gly Ser Pro Asp
         -1   1              5                  10

Pro Asp Ser Thr Gly Ala Leu Val Glu Glu Asp Pro Phe Phe Lys
    15              20                  25

Val Pro Val Asn Lys Leu Ala Ala Ala Val Ser Asn Phe Gly Tyr Asp
30                  35                  40                  45

Leu Tyr Arg Val Arg Ser Ser Thr Ser Pro Thr Thr Asn Val Leu Leu
                50                  55                  60

Ser Pro Leu Ser Val Ala Thr Ala Leu Ser Ala Leu Ser Leu Gly Ala
             65                  70                  75

Glu Gln Arg Thr Glu Ser Ile Ile His Arg Ala Leu Tyr Tyr Asp Leu
             80                  85                  90

Ile Ser Ser Pro Asp Ile His Gly Thr Tyr Lys Glu Leu Leu Asp Thr
95                  100                 105

Val Thr Ala Pro Gln Lys Asn Leu Lys Ser Ala Ser Arg Ile Val Phe
110                 115                 120                 125

Glu Lys Lys Leu Arg Ile Lys Ser Ser Phe Val Ala Pro Leu Glu Lys
                130                 135                 140

Ser Tyr Gly Thr Arg Pro Arg Val Leu Thr Gly Asn Pro Arg Leu Asp
             145                 150                 155

Leu Gln Glu Ile Asn Asn Trp Val Gln Ala Gln Met Lys Gly Lys Leu
             160                 165                 170

Ala Arg Ser Thr Lys Glu Ile Pro Asp Glu Ile Ser Ile Leu Leu Leu
    175                 180                 185

Gly Val Ala His Phe Lys Gly Gln Trp Val Thr Lys Phe Asp Ser Arg
190                 195                 200                 205

Lys Thr Ser Leu Glu Asp Phe Tyr Leu Asp Glu Glu Arg Thr Val Arg
                210                 215                 220

Val Pro Met Met Ser Asp Pro Lys Ala Val Leu Arg Tyr Gly Leu Asp
             225                 230                 235

Ser Asp Leu Ser Cys Lys Ile Ala Gln Leu Pro Leu Thr Gly Ser Met
             240                 245                 250

Ser Ile Ile Phe Phe Leu Pro Leu Lys Val Thr Gln Asn Leu Thr Leu
    255                 260                 265

Ile Glu Glu Ser Leu Thr Ser Glu Phe Ile His Asp Ile Asp Arg Glu
270                 275                 280                 285

Leu Lys Thr Val Gln Ala Val Leu Thr Val Pro Lys Leu Lys Leu Ser
                290                 295                 300

Tyr Glu Gly Glu Val Thr Lys Ser Leu Gln Glu Met Lys Leu Gln Ser
             305                 310                 315

Leu Phe Asp Ser Pro Asp Phe Ser Lys Ile Thr Gly Lys Pro Ile Lys
             320                 325                 330

Leu Thr Gln Val Glu His Arg Ala Gly Phe Glu Trp Asn Glu Asp Gly
    335                 340                 345

Ala Gly Thr Thr Pro Ser Pro Gly Leu Gln Pro Ala His Leu Thr Phe
350                 355                 360                 365

-continued

```
Pro Leu Asp Tyr His Leu Asn Gln Pro Phe Ile Phe Val Leu Arg Asp
            370                 375                 380

Thr Asp Thr Gly Ala Leu Leu Phe Ile Gly Lys Ile Leu Asp Pro Arg
            385                 390                 395

Gly Pro
```